United States Patent
Hao et al.

(10) Patent No.: US 9,682,954 B2
(45) Date of Patent: Jun. 20, 2017

(54) PHENANTHRIDINE DERIVATIVES, PREPARATION METHODS AND USES THEREOF

(71) Applicants: Kunming Institute of Botany, The Chinese Academy of Sciences, Kunming, Yunnan (CN); Shanghai Institutes for Biological Sciences, CAS, Shanghai (CN); Institute of Medicinal Biotechnology, Chinese Academy of Medical Sciences, Beijing (CN)

(72) Inventors: Xiaojiang Hao, Yunnan (CN); Duozhi Chen, Yunnan (CN); Lin Li, Shanghai (CN); Zonggen Peng, Beijing (CN); Jiandong Jiang, Beijing (CN); Yingtong Di, Yunnan (CN); Junlin Yin, Yunnan (CN); Sheng Wang, Shanghai (CN); Jieyun Cai, Yunnan (CN)

(73) Assignees: Kunming Institute of Botany, The Chinese Academy of Sciences, Yunnan (CN); Shanghai Institutes for Biological Sciences, CAS, Shanghai (CN); Institute of Medicinal Biotechnology, Chinese Academy of Medical Sciences, Beijing (CN)

( * ) Notice: Subject to any disclaimer, the term of this patent is extended or adjusted under 35 U.S.C. 154(b) by 0 days.

(21) Appl. No.: 14/770,923

(22) PCT Filed: Feb. 28, 2014

(86) PCT No.: PCT/CN2014/072697
§ 371 (c)(1),
(2) Date: Dec. 4, 2015

(87) PCT Pub. No.: WO2014/131368
PCT Pub. Date: Sep. 4, 2014

(65) Prior Publication Data
US 2016/0083364 A1 Mar. 24, 2016

(30) Foreign Application Priority Data

Mar. 1, 2013 (CN) .......................... 2013 1 0066012
Mar. 13, 2013 (CN) .......................... 2013 1 0080161

(51) Int. Cl.
*C07D 401/12* (2006.01)
*A61K 31/473* (2006.01)
*C07D 221/12* (2006.01)

(52) U.S. Cl.
CPC .......... *C07D 401/12* (2013.01); *A61K 31/473* (2013.01); *C07D 221/12* (2013.01)

(58) Field of Classification Search
CPC .......................... C07D 401/12; A61K 31/473
USPC .......................................................... 546/79
See application file for complete search history.

(56) References Cited

U.S. PATENT DOCUMENTS

2012/0316342 A1   12/2012   Baba et al.

FOREIGN PATENT DOCUMENTS

| CN | 102812007 | 12/2012 |
| CN | 103113353 | 5/2013 |
| CN | 103145617 | 6/2013 |
| JP | 56-118069 | 9/1981 |

OTHER PUBLICATIONS

Juan Cedron et al Synthesis and antiplasmodial activity of lycorine derivatives. 2010.*
Cedron et al , Synthesis and antiplasmodial activity of lycorine derivatives, Jul. 2010.*
Cedron et al., "Synthesis and antiplasmodial activity of lycorine derivatives", Bioorganic & Medicinal Chemistry, 18 (13):4694-4701, 2010.
Wang et al., "Small-molecule modulation of Wnt signaling via modulating the Axin-LRP5/6 interaction", Nature Chemical Biology, 9(9):579-583, 2013.
Ferraccioli et al., "Synthesis of 6-Phenanthridinones and Their Heterocyclic Analogues through Palladium-Catalyzed Sequential Aryl-Aryl and N-Aryl Coupling", Organic Letters, 6(25):4759-4762, 2004.

* cited by examiner

*Primary Examiner* — Rita Desai
(74) *Attorney, Agent, or Firm* — Honigman Miller Schwartz and Cohn LLP; Thomas A. Wootton; Jonathan P. O'Brien

(57) ABSTRACT

The present invention relates to the pharmaceutical field, in particular to a phenanthridine derivative as shown in general formula (1)

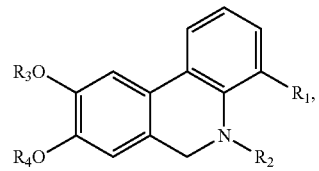

a pharmaceutical composition comprising the derivative, its preparation method, and its uses in manufacture of a medicament for the prevention or treatment of a disease related to the activity of Wnt signaling pathway, hepatitis C and hepatitis B.

8 Claims, 1 Drawing Sheet

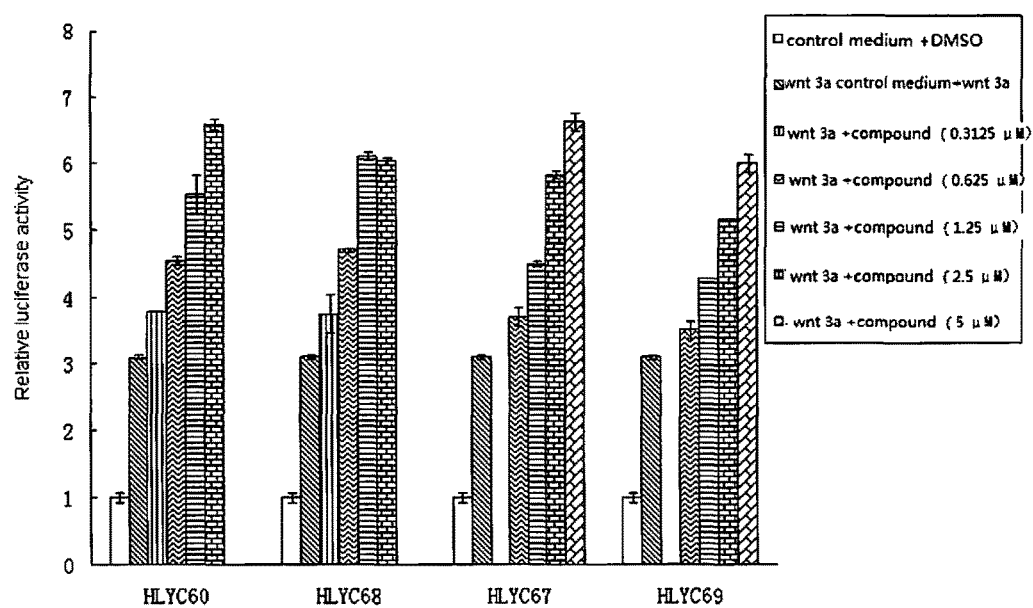

PHENANTHRIDINE DERIVATIVES, PREPARATION METHODS AND USES THEREOF

CROSS-REFERENCE TO RELATED APPLICATIONS

This application claims priority under 35 U.S.C. §371 to Patent Cooperation Treaty Application PCT/CN2014/072697, filed Feb. 28, 2014, which claims the benefit of Chinese Patent Application No. 201310080161.1, filed Mar. 13, 2013, which claims the benefit of Chinese Patent Application No. 201310066012.X, filed Mar. 1, 2013, the entire contents of which are incorporated herein by reference.

TECHNICAL FIELD

The present invention relates to the pharmaceutical field, in particular to a phenanthridine derivative, a pharmaceutical composition comprising the derivative, its preparation method, and its uses in manufacture of a medicament for prevention or treatment of a disease related to the activity of Wnt signaling pathway, hepatitis C and hepatitis B.

BACKGROUND

World Health Organization estimates that there are about 2 billion patients infected with hepatitis B virus in the world, and 0.35-0.4 billion of them are chronic patients infected with HBV. Deaths due to acute or chronic HBV infection have reached 113.13 million every year and are increasing. There are a large number of hepatitis B patients in China and account for one-third of the number of chronic patients infected with HBV of the world, wherein, there are 0.12 billion hepatitis B carriers. Data shows that infection of hepatitis B virus has become a major disease endangering human health, therefore, an anti-HBV therapy effective in patients infected with HBV is particularly in urgent need worldwide, especially in China. In studies about treatment of HBV infection at home and abroad, it is considered that, persistent infection of HBV is the main reason for hepatitis B chronicity, and may lead to progression and deterioration of the disease into cirrhosis or HBV related hepatocellular carcinoma. Therefore, inhibition of HBV replication is the key to the treatment of chronic hepatitis B. At present, main drugs used for treatment of hepatitis B clinically can mainly be divided, according to their structures, sources and functions, into interferons, nucleosides, immunomodulators and natural herbs.

Hepatitis C virus (HCV) is a major cause for chronic liver diseases. There is no vaccine used for preventing HCV infection. The combination of long-term PEG IFN-α and Ribavirin (RBV) is the best drug used for treatment of hepatitis C in recent 10 years, but more than 50% of patents infected with type I HCV failed to respond to such combinational antiviral therapy. Moreover, IFN and RBV have great toxic and side effects and the course of treatment is up to 1 year, which greatly limite its clinical use. Meanwhile, some anti-HCV medicaments inhibiting protease NS3/NS5 are also in clinical trials in recent years.

Wnt signaling pathways are highly evolutionarily conserved in organism and regulate many life courses. During early development of animals, Wnt signaling is responsible for a series of important events such as ventral axis formation, blastoderm establishment, somite differentiation, tissue or organ formation, and directly controls cell fates such as proliferation, differentiation, polarization, apoptosis and anti-apoptosis. More than 10 members of the Wnt proteins are involved in various signal transduction pathways via interacting with different receptors on cell membrane. These pathways are divided into classical Wnt signaling pathway depending on β-catenin/TCF transcription complex (Wnt/β-catenin pathway) and non-classical Wnt signaling pathway independing on β-catenin/TCF transcription complex (Wnt/$Ca^{2+}$ pathway and Wnt/JNK pathway).

Because Wnt/β-catenin signaling pathway is associated with many cancers and diseases, regulation of uncontrolled Wnt/β-catenin signaling pathway can be an excellent means for treating diseases related to Wnt/β-catenin signaling pathway. For example, the pathologic process of Alzheimer's disease is accompanied by abnormal inactivation of Wnt/β-catenin signaling pathway. Presenilin associated closely with Alzheimer's disease can form a complex with β-catenin and GSK3. Hence, molecular targeted therapies directed to the signaling pathways are expected to be a new and effective way for treatment of related diseases. In addition, Wnt signaling pathway also functions in maintaining pluripotency of stem cells, so adjustments of the signaling pathway are expected to be a new and effective way for application of stem cells.

Therefore, it is in urgent need to develop new drugs for treatment of hepatitis B, hepatitis C, and diseases associated with activity of Wnt signaling pathway.

CONTENTS OF THE INVENTION

The invention aims at providing a phenanthridine derivative having an effect of activation of Wnt signaling pathway, anti-hepatitis B or anti-hepatitis C, a pharmaceutical composition comprising the phenanthridine derivative as an active agent, its preparation method, and its use in preparing a medicament.

The first aspect of the invention relates to a compound of general formula (1)

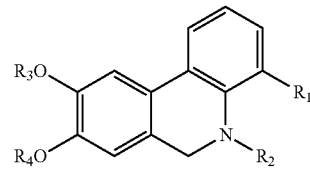

or a stereo isomer, a solvate, a pharmaceutically acceptable salt thereof, wherein, $R_1$ is selected from $C_1$-$C_6$alkyl or $C_1$-$C_6$alkenyl;
$R_2$ is selected from hydrogen, $C_1$-$C_6$alkyl;
$R_3$ or $R_4$ is selected from hydrogen, $C_1$-$C_6$alkyl, $C_1$-$C_6$alkenyl, benzyl, silyl, $C_1$-$C_6$alkanoyl, benzoyl, 1-(amino-$C_{1-6}$alkyl)-1H-[1,2,3]triazol-4-methyl, which is unsubstituted or substituted by a substituent, wherein the substituent is selected from $C_1$-$C_6$alkyl, $C_1$-$C_6$alkoxy, halo, $C_1$-$C_6$alkanoyl, the number of the substituent is one, two or three.

The compound of general formula (1) according to any item of the first aspect of the invention, wherein $R_1$ is selected from methyl, ethyl, and vinyl.

The compound of general formula (1) according to any item of the first aspect of the invention, wherein $R_2$ is selected from H, methyl and ethyl.

The compound of general formula (1) according to any item of the first aspect of the invention, wherein, $R_3$ or $R_4$ is selected from H, methyl, propyl, isopropyl, propenyl, n-butyl, isobutyl, tert-butyl, cyclopropylmethyl, cyclobutylmethyl, cyclohexylmethyl, benzyl, 2,3-dimethoxybenzyl; 3,5-dimethoxybenzyl, tert-butyldimethylsilyl, trimethylsilyl; acetyl, propionyl, butyryl, isobutyryl, valeryl, isovaleryl, benzoyl, p-methoxybenzoyl, 3-methoxybenzoyl, bromobenzoyl, chlorobenzoyl, 3,5-dimethoxybenzoyl, 2,3-dimethoxybenzoyl, 3,4,5-trimethoxybenzoyl, 1-(2-amino-ethyl)-1H-[1,2,3]triazol-4-methyl, 1-(2-acetylamino-ethyl)-1H-[1,2,3]triazol-4-methyl.

In an embodiment of the invention, $R_1$ is selected from —$CH_3$, —$CH_2CH_3$,

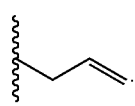 [SMILES: *CC=C]

In an embodiment of the invention, $R_2$ is selected from H, —$CH_3$, —$CH_2CH_3$.

In an embodiment of the invention, $R_3$ or $R_4$ is selected from H, —$CH_3$, —$CH_2CH_3$,

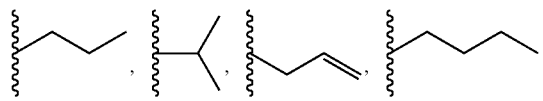

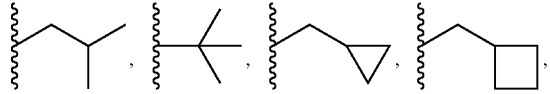

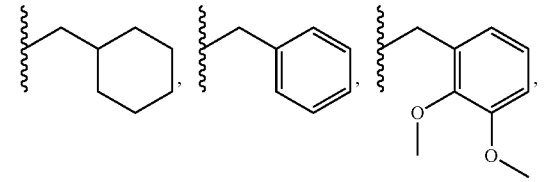

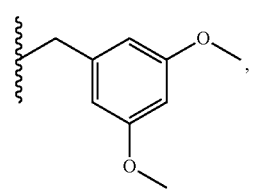

tert-butyldimethylsilyl, trimethylsilyl, —Ac,

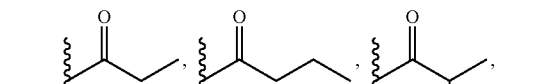

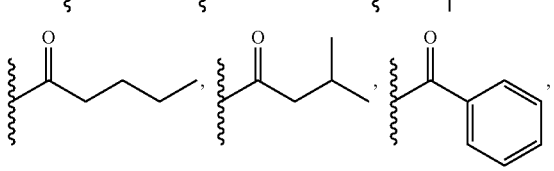

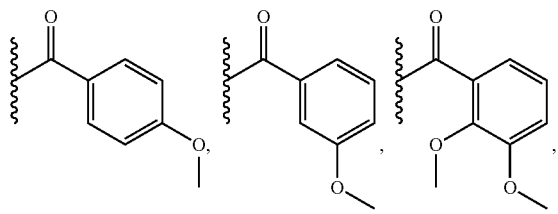

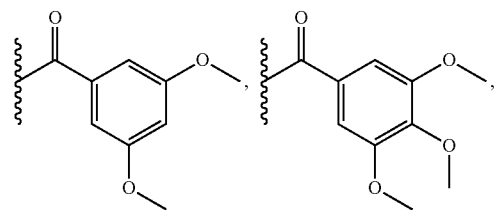

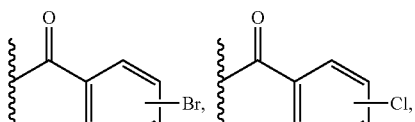

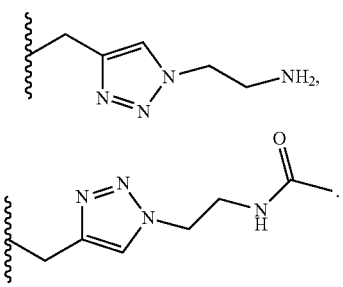

The second aspect of the invention relates to a compound of general formula (2)

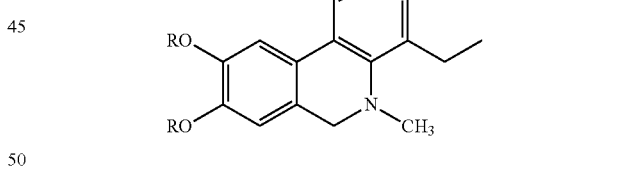

or a stereo isomer, a solvate, a pharmaceutically acceptable salt thereof, wherein, R is selected from H, methyl, ethyl, propyl, isopropyl, propenyl, n-butyl, isobutyl, tert-butyl, cyclopropylmethyl, cyclobutylmethyl, cyclohexylmethyl, benzyl, 2,3-dimethoxybenzyl; 3,5-dimethoxybenzyl, tert-butyldimethylsilyl, trimethylsilyl; acetyl, propionyl, butyryl, isobutyryl, valeryl, isovaleryl, benzoyl, p-methoxybenzoyl, 3-methoxybenzoyl, bromobenzoyl, chlorobenzoyl, 3,5-dimethoxybenzoyl, 2,3-dimethoxybenzoyl, 3,4,5-trimethoxybenzoyl, 1-(2-amino-ethyl)-1H-[1,2,3]triazol-4-methyl, 1-(2-acetylamino-ethyl)-1H-[1,2,3]triazol-4-methyl.

The compound of general formula (2) according to any item of the second aspect of the invention, which is selected from compounds as follows,

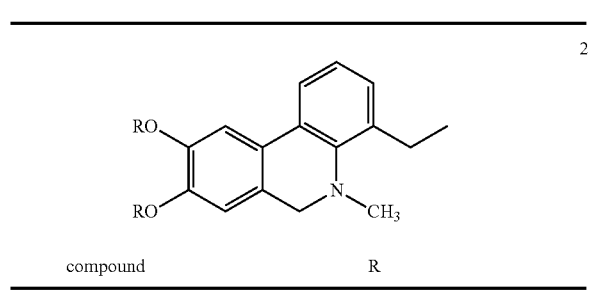

| compound | R |
|---|---|
| 10 | H |
| 10a | —CH₃ |
| 10b | —CH₂CH₃ |
| 10c | (allyl) |
| 10d | (propargyl) |
| 10e | (cyclobutylmethyl) |
| 10f | (cyclohexylmethyl) |
| 10g | (benzyl) |
| 10h | (2,3-dimethoxybenzyl) |
| 10j | Ac |
| 10k | (propionyl) |
| 10l | (isobutyryl) |
| 10m | (valeryl) |
| 10n | (isovaleryl) |
| 10o | (benzoyl) |
| 10p | (4-bromobenzoyl) |
| 10q | (1-(2-aminoethyl)-triazol-4-methyl) |
| 10r | (1-(2-acetylaminoethyl)-triazol-4-methyl) |

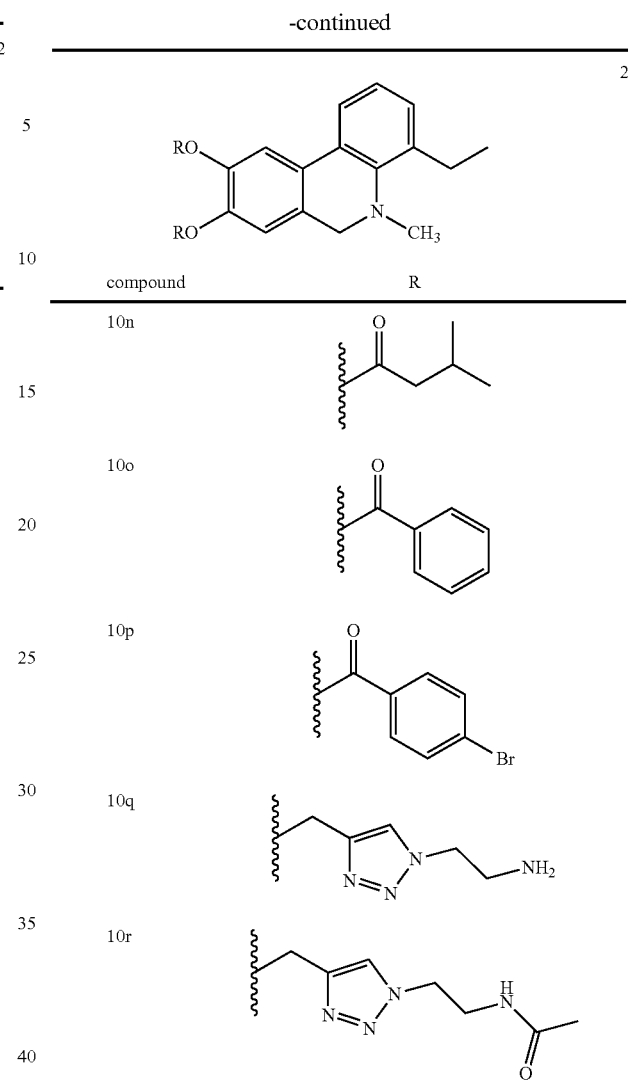

The third aspect of the invention relates to a compound of general formula (3), or a stereo isomer, a solvate, a pharmaceutically acceptable salt thereof, Wherein, R is selected from propyl, isopropyl, propenyl, n-butyl, isobutyl, tert-butyl, cyclopropylmethyl, cyclobutylmethyl, cyclohexylmethyl, benzyl, 2,3-dimethoxybenzyl; 3,5-dimethoxybenzyl, tert-butyldimethylsilyl, trimethylsilyl; acetyl, propionyl, butyryl, isobutyryl, valeryl, isovaleryl, benzoyl, p-methoxybenzoyl, 3-methoxybenzoyl, bromobenzoyl, chlorobenzoyl, 3,5-dimethoxybenzoyl, 2,3-dimethoxybenzoyl, 3,4,5-trimethoxybenzoyl, 1-(2-amino-ethyl)-1H-[1,2,3]triazol-4-methyl, and 1-(2-acetylamino-ethyl)-1H-[1,2,3]triazol-4-methyl.

The compound of general formula (3) according to any one of the third aspect of the invention, which is selected from compounds as follows,

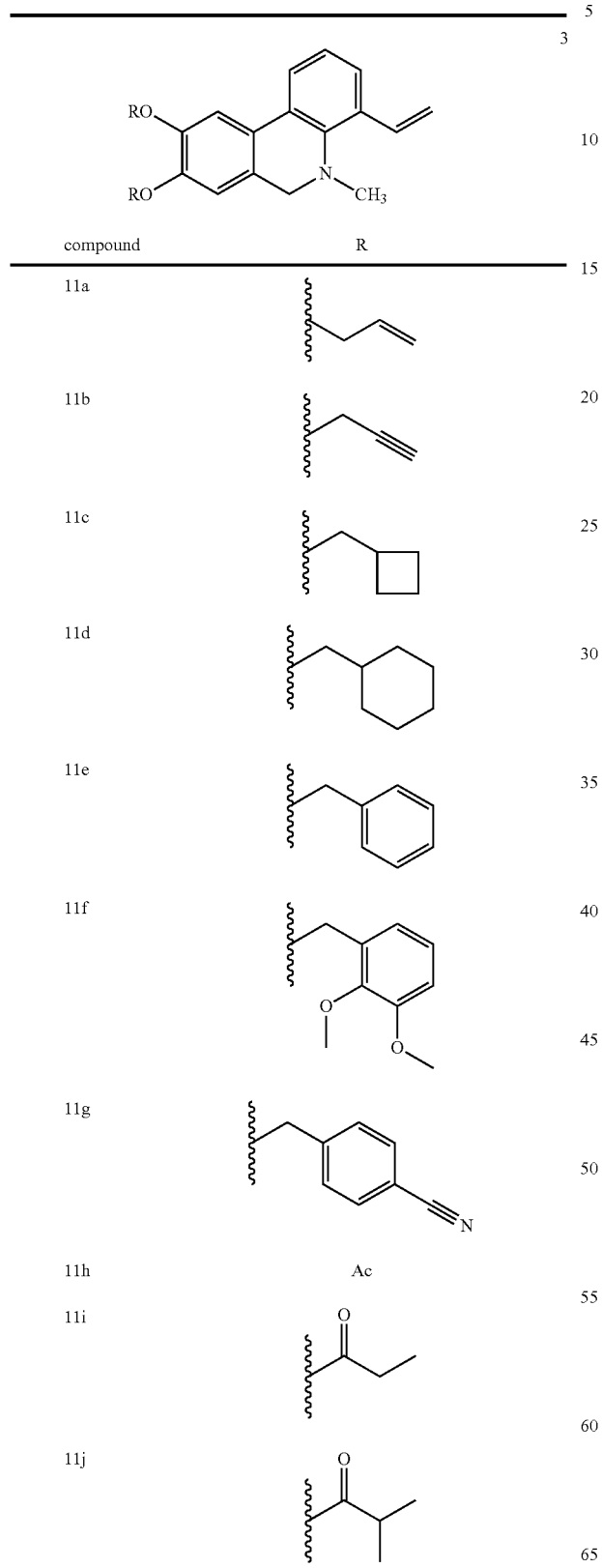

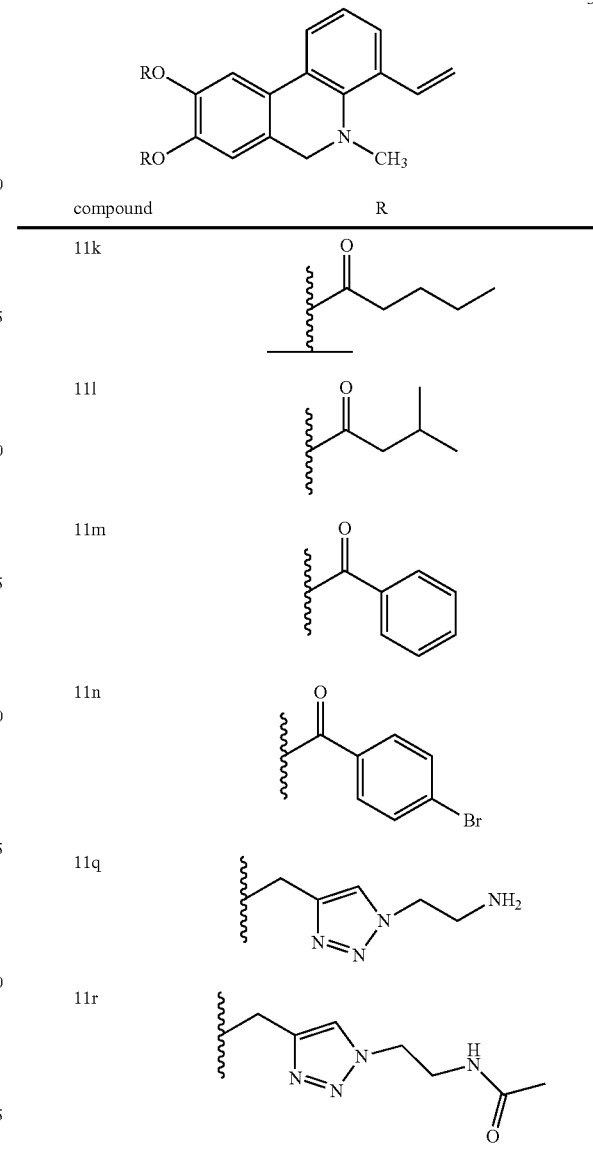

The compound according to any item of the first aspect to the third aspect of the invention, wherein the compound is selected from the following compounds:
4-ethyl-5-methyl-5H-8,9-dimethoxyphenanthridin-6-one (15);
4-ethyl-5-methyl-5,6-dihydro-phenanthridine-8,9-diol (10);
4-ethyl-5-methyl-8,9-dimethoxy-5,6-dihydro-phenanthridine (10a);
4-ethyl-5-methyl-8,9-diethyoxy-5,6-dihydro-phenanthridine (10b);
4-ethyl-5-methyl-8,9-diallyloxy-5,6-dihydro-phenanthridine (10c);
4-ethyl-5-methyl-8,9-diprop-2-ynyloxy-5,6-dihydro-phenanthridine (10d);
4-ethyl-5-methyl-8,9-bis-cyclobutylmethoxy-5,6-dihydro-phenanthridine (10e);
4-ethyl-5-methyl-8,9-bis-cyclobutylmethoxy-5,6-dihydro-phenanthfidine (10f);
4-ethyl-5-methyl-8,9-dibenzyloxy-5,6-dihydro-phenanthridine (10g);

4-ethyl-5-methyl-8,9-di(2,3-dimethoxy)benzyloxy-5,6-dihydro-phenanthridine (10h);
4-ethyl-5-methyl-8-9-diacetoxy-5,6-dihydro-phenanthridine (10j);
4-ethyl-5-methyl-8,9-dipropionyloxy-5,6-dihydro-phenanthridine (10k);
4-ethyl-5-methyl-8,9-diisobutyryloxy-5,6-dihydro-phenanthridine (10l);
4-ethyl-5-methyl-8,9-divaleryoxy-5,6-dihydro-phenanthridine (10m);
4-ethyl-5-methyl-8,9-diisovaleroxy-5,6-dihydro-phenanthridine (10n);
4-ethyl-5-methyl-8,9-dibenzoyloxy-5,6-dihydro-phenanthridine (10o);
4-ethyl-5-methyl-8,9-di(4-bromo)benzoyloxy-5,6-dihydro-phenanthridine (10p);
4-ethenyl-5-methyl-5,6-dihydrophenanthridine-8,9-diol (11);
4-ethenyl-5-methyl-8,9-diallyloxy-5,6-dihydro-phenanthridine (11a);
4-ethenyl-5-methyl-8,9-di(prop-2-ynyloxy)-5,6-dihydro-phenanthridine (11b);
4-ethenyl-5-methyl-8,9-bis-cyclobutylmethoxy-5,6-dihydro-phenanthridine (11c);
4-ethenyl-5-methyl-8,9-bis-cyclohexylmethoxy-5,6-dihydro-phenanthridine (11d);
4-ethenyl-5-methyl-8,9-dibenzyloxy-5,6-dihydro-phenanthridine (11e);
4-ethenyl-5-methyl-8,9-di(2,3-dimethoxy)benzyloxy-5,6-dihydro-phenanthridine (11 f);
4-ethenyl-5-methyl-8,9-di(4-cyano)benzyloxy-5,6-dihydro-phenanthridine (11g);
4-ethenyl-5-methyl-8,9-diacetoxy-5,6-dihydro-phenanthridine (11 h);
4-ethenyl-5-methyl-8,9-dipropionyloxy-5,6-dihydro-phenanthridine (11i);
4-ethenyl-5-methyl-8,9-diisobutyryloxy-5,6-dihydro-phenanthridine (11j);
4-ethenyl-5-methyl-8,9-divaleryoxy-5,6-dihydro-phenanthridine (11k);
4-ethenyl-5-methyl-8,9-diisovaleroxy-5,6-dihydro-phenanthridine (11l);
4-ethenyl-5-methyl-8,9-dibenzoyloxy-5,6-dihydro-phenanthridine (11m);
4-ethenyl-5-methyl-8,9-di(4-bromo)benzoyloxy-5,6-dihydro-phenanthridine (11n);
4-ethyl-5-methyl-8,9-bis[1-(2-amino-ethyl)-1H-[1,2,3]triazol-4-ylmethoy]-5,6-dihydro-phenanthridine (10q);
4-ethyl-5-methyl-8,9-bis[1-(2-acetylamino-ethyl)-1H-[1,2,3]triazol-4-ylmethoxy]-5,6-dihydro-phenanthridine (10r);
4-ethenyl-5-methyl-8,9-bis[1-(2-amino-ethyl)-1H-[1,2,3]triazol-4-ylmethoxy]-5,6-dihydro-phenanthridine (11q);
4-ethenyl-5-methyl-8,9-bis[1-(2-acetylamino-ethyl)-1H-[1,2,3]triazol-4-ylmethoxy]-5,6-dihydro-phenanthridine (11r);
5-methyl-4-vinyl-5,6-dihydro-[1,3]dioxolo[4,5-j]phenanthridine (8);
4-ethyl-5-methyl-5,6-dihydro-[1,3]dioxolo[4,5-j]phenanthridine (9);
2-bromo-4,5-dimethoxy-benzoic acid (13);
2-bromo-4,5-dimethoxy-N-methyl-benzamide (14);
2-bromo-4,5-dimethoxy-benzaldehyde (12).

The present invention further relates to a pharmaceutical composition, comprising a prophylactically or therapeutically effective amount of the compound according to any item of the first aspect to the third aspect of the invention, and a pharmaceutically acceptable carrier or excipient.

The present invention further relates to a method of preparing the compound according to any item of the first aspect to the third aspect of the invention, comprising the following steps:

1) the compound is prepared through N-methylation, Hofmann degradation, catalytic hydrogenation, and degradation of dioxomethylene group, as well as alkylation and acylation of phenolic hydroxyl group, by using lycorine hydrochloride as a starting material; or 2) the compound is prepared through oxidation, coupling, LAH reduction, and demethylation, by using 2-bromo-4,5-dimethoxybenzaldehyde and 2-ethyl-iodobenzene or 2-vinyl-iodobenzene as starting materials.

In an embodiment of the invention, the reaction process is:

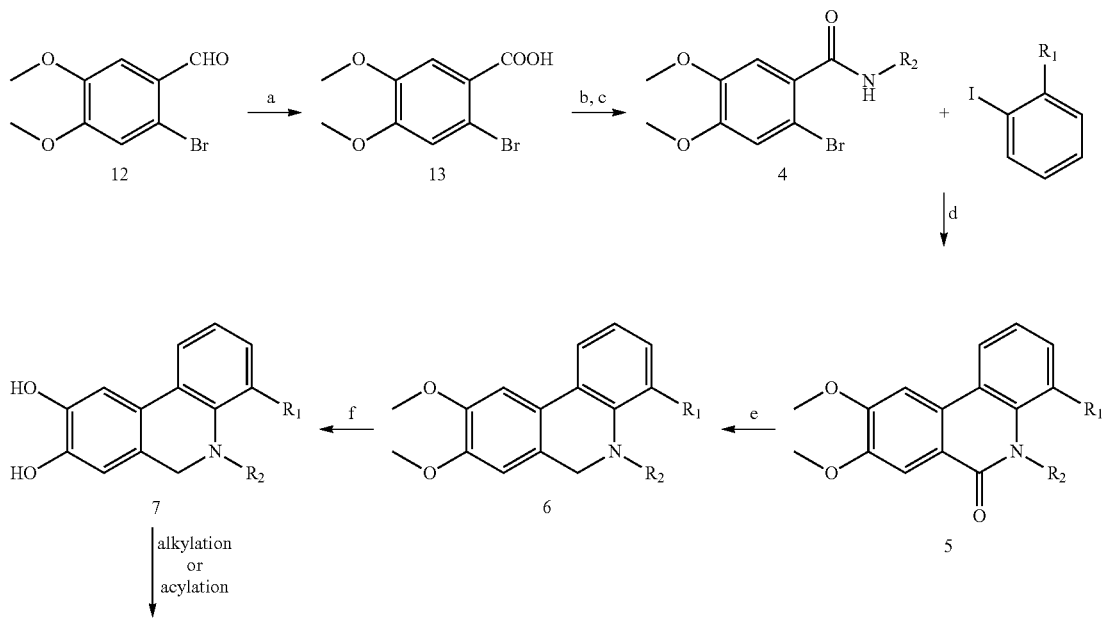

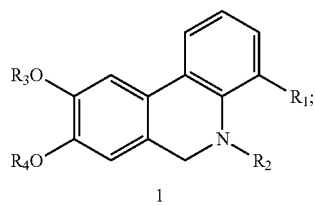

preferably, reagents and conditions are: a) NaHCO$_3$, KMnO$_4$, H$_2$O, 90° C., 3 h, 85%; b) SOCl$_2$, DMF, THF, 50° C., 2 h; c) R$_2$NH$_2$ (30%), 5° C., 1 h, 75%; d) K$_2$CO$_3$, norbornene, Pd(OAc)$_2$, TFP, MeCN, 85° C., 6 h, 75%; e) LAH, THF, −78° C., 2 h, 60%; f) BBr$_3$, CH$_2$Cl$_2$, 78° C., 4 h, 80%.

In an embodiment of the invention, the reaction process is:

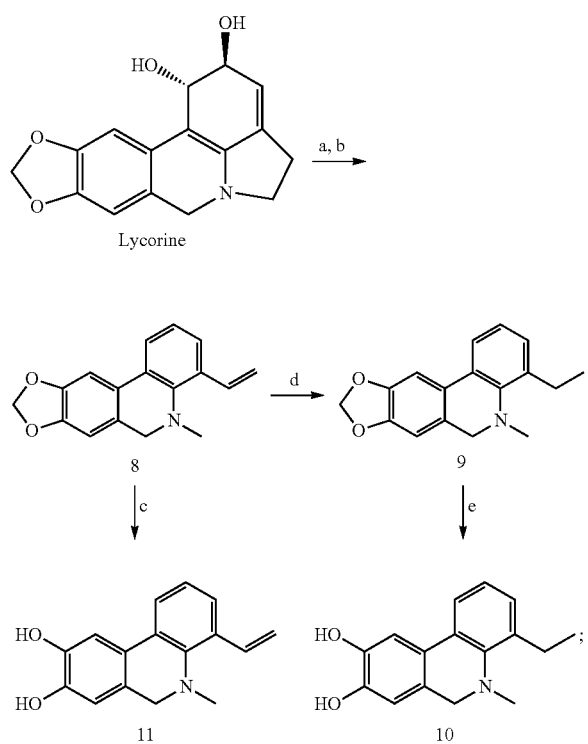

preferably, reagents and conditions are: a) CH$_3$I, r.t., 12 h; b) KTB, TBA, 90° C., 4 h, 90%; c) BBr$_3$, CH$_2$Cl$_2$, −78° C., 6 h, 65%; d) 10% Pb/C, H$_2$, 24 h, 95%; e) BBr$_3$, CH$_2$Cl$_2$, −78° C., 10 h, 72%.

The present invention further relates to a method for preparing the compound according to any item of the first aspect to the third aspect of the present invention, comprising the following steps:

1) intermediate 8 is prepared through N-methylation and Hofmann degradation using lycorine as a starting material, and separated;

2) intermediate 11 is prepared by degrading dioxomethylene group of compound 8, and separated;

3) compound 9 is prepared by hydrogenation reduction of intermediate 8, and separated 4) intermediate 10 is prepared by degrading the dioxomethylene group of compound 9, and separated;

5) compounds 11b and 10d are prepared by alkylation of compounds 11 and 10 respectively with 3-bromo-propyne, and separated;

6) compounds 11b and 10d are respectively reacted with general formula 21 through Click reaction to prepare compounds of general formula 17 and 18;

7) compounds of formula 19 and formula 20 are obtained by acylation of compounds of formula 17 and formula 18 with C$_1$-C$_6$ anhydride respectively, and separated;

wherein in the formula, R, R$_3$ or R$_4$ is 1-(amino-C$_{1-6}$alkyl)-1H-[1,2,3]triazol-4-methyl, which is unsubstituted or substituted by a substituent, wherein the substituent is C$_1$-C$_6$alkanoyl, or said compound is compound 8 or 9, preferably, said R, R$_3$ or R$_4$ is 1-(2-amino-ethyl)-1H-[1,2,3]triazol-4-methyl or 1-(2-acetylamino-ethyl)-1H-[1,2,3]triazol-4-methyl, wherein n is 1-6 (for example, 1, 2, 3, 4, 5, 6);

in particular, the method comprising the following steps:

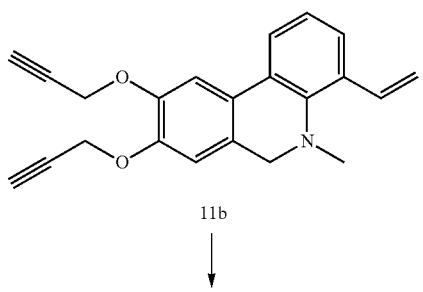

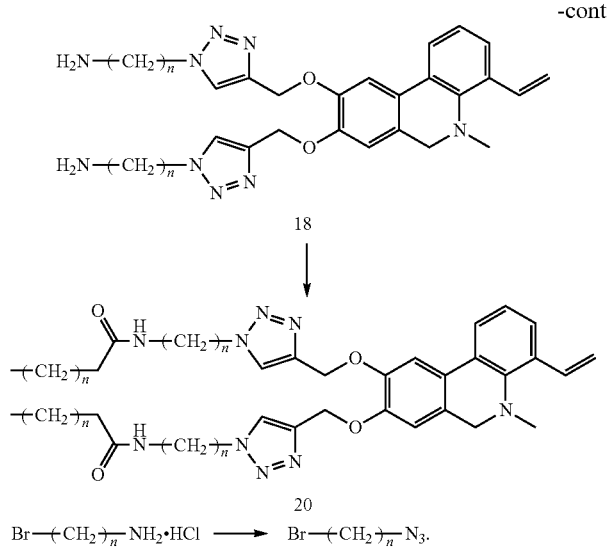

18

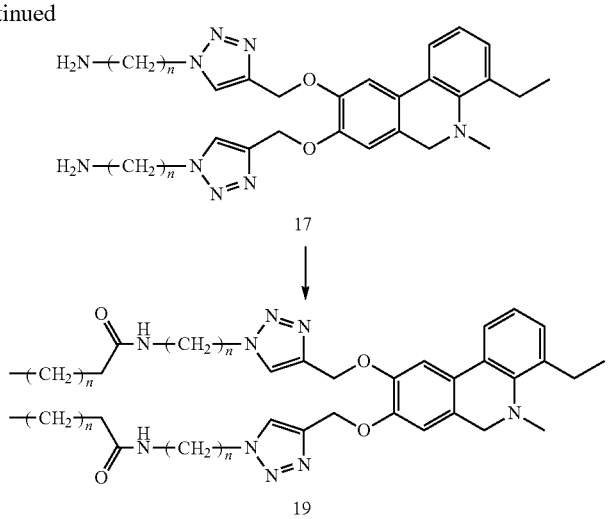

17

20

19

Br―(CH₂)ₙ―NH₂·HCl ⟶ Br―(CH₂)ₙ―N₃.

21

The present invention further relates to use of the compound according to any item of the first aspect to the third aspect of the invention in manufacture of a medicament for defending against virus (for example hepatitis B virus or hepatitis C virus).

The present invention further relates to use of the compound according to any item of the first aspect to the third aspect of the invention in manufacture of a medicament for prevention or treatment of hepatitis B or hepatitis C.

In the present invention, the hepatitis B or the hepatitis C refers to acute or chronic hepatitis B or hepatitis C.

The present invention further relates to use of the compound according to any item of the first aspect to the third aspect of the invention in manufacture of a medicament for prophylaxis or treatment of a disease or disorder caused by abnormal inactivation of classical Wnt signaling pathway, wherein in the general formula, R, $R_3$ or $R_4$ is 1-(amino-$C_{1-6}$alkyl)-1H-[1,2,3]triazol-4-methyl, which is unsubstituted or substituted by a substitutent, wherein the substituent is $C_1$-$C_6$alkanoyl, or said compound is compound 8 or 9.

In an embodiment of the invention, said R, $R_3$ or $R_4$ is 1-(2-amino-ethyl)-1H-[1,2,3]triazol-4-methyl or 1-(2-acetylamino-ethyl)-1H-[1,2,3]triazol-4-methyl.

In an embodiment of the invention, said disease or disorder caused by abnormal inactivation of classical Wnt signaling pathway includes senile dementia (Alzheimer's disease), rheumatoid arthritis, osteoporosis, cancer or zebrafish development disorder.

The present invention further relates to use of the compound according to any item of the first aspect to the third aspect of the invention in preparing an agonist of classical Wnt signaling pathway or a medicament for stem cells proliferation, wherein in the formula, R, $R_3$ or $R_4$ is 1-(amino-$C_{1-6}$alkyl)-1H-[1,2,3]triazol-4-methyl, unsubstituted or substituted by a substitutent, wherein the substituent is $C_1$-$C_6$alkanoyl, or said compound is compound 8 or 9.

In an embodiment of the invention, R, $R_3$ or $R_4$ is 1-(2-amino-ethyl)-1H-[1,2,3]triazol-4-methyl or 1-(2-acetylamino-ethyl)-1H-[1,2,3]triazol-4-methyl.

In the present invention, the agonist of classical Wnt signaling pathway is able to activate expression of the reporter gene or interest gene of classical Wnt signaling pathway.

The present invention further relates to a method of defending against virus (e.g. hepatitis B virus or hepatitis C virus), comprising the step of administering to a subject in need an effective amount of the compound according to any item of the first aspect to the third aspect of the invention.

The present invention further relates to a method of prevention or treatment of hepatitis B or hepatitis C, comprising the step of administering to a subject in need a prophylactically or therapeutically effective amount of the compound according to any item of the first aspect to the third aspect of the invention.

The present invention further relates to a method for prevention or treatment of a disease or disorder caused by abnormal inactivation of classical Wnt signaling pathway, comprising the step of administering to a subject in need a prophylactically or therapeutically effective amount of the compound according to any item of the first aspect to the third aspect of the invention, wherein in the general formula, R, $R_3$ or $R_4$ is 1-(amino-$C_{1-6}$alkyl)-1H-[1,2,3]triazol-4-methyl, which is unsubstituted or substituted by a substitutent, wherein the substituent is $C_1$-$C_6$alkanoyl, or said compound is compound 8 or 9.

In an embodiment of the invention, R, $R_3$ or $R_4$ is 1-(2-amino-ethyl)-1H-[1,2,3]triazol-4-methyl or 1-(2-acetylamino-ethyl)-1H-[1,2,3]triazol-4-methyl.

In an embodiment of the invention, the disease or disorder caused by abnormal inactivation of classical Wnt signaling pathway comprises senile dementia (Alzheimer's disease), rheumatoid arthritis, osteoporosis, or zebrafish development disorder.

In the present invention, the term "$C_1$-$C_6$alkyl" means straight, branched or cyclic alkyl having 1 to 6 (e.g. 1-3) carbon atoms, including but not limited to methyl, ethyl, n-propyl, isopropyl, n-butyl, sec-butyl, isobutyl, tertiary butyl, pentyl, neopentyl, hexyl, cyclopropyl, cyclobutyl, cyclopentyl, cyclohexyl and the like.

In the present invention, the term "$C_1$-$C_6$alkenyl" means straight or branched aliphatic hydrocarbon having 1-6 (e.g. 1-3) carbon atoms and carbon-carbon double bond, including but not limited to, vinyl, propenyl, n-butenyl, isobutenyl, 3-methyl-but-2-enyl, n-pentenyl, cyclohexylbutenyl and the like.

In the present invention, said $C_1$-$C_6$alkanoyl refers to $C_1$-$C_6$alkyl-CO—, wherein $C_1$-$C_6$alkyl is as described herein, such as acetyl, propionyl, butanoyl, isobutyryl, valeryl, isovaleryl.

In the present invention, said $C_1$-$C_6$alkoxy refers to $C_1$-$C_6$alkyl-O—, wherein $C_1$-$C_6$alkyl is as described herein, such as methoxy, ethoxy.

In the present invention, said 1-(amino-$C_{1-6}$alkyl)-1H-[1,2,3]triazol-4-methyl means

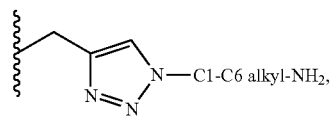

wherein $C_1$-$C_6$ alkyl is as described herein.

In the present invention, said $C_1$-$C_6$alkanoyl refers to $C_1$-$C_6$alkyl-CO—, wherein $C_1$-$C_6$alkyl is as described herein, such as formyl, acetyl, propionyl.

The inventor found that benzylphenethylamine alkaloids has an activity against a variety of virus when studying anti-virus natural products of plant, and through structure modification, structure-activity relationships, and structural optimization, it is found that the phenanthridine derivative shows significant functions of activating Wnt signaling pathway, and anti-hepatitis B virus and anti-hepatitis C virus.

When the compound of the present invention is used as medicament, it can be used directly, or used in the form of a pharmaceutical composition. The pharmaceutical composition comprises 0.1-99.5%, preferably 0.5-90% of the compound of the present invention, and the rest is a pharmaceutically acceptable pharmaceutical carrier and/or excipient which is non-toxic to human and animal and is inert.

The pharmaceutical carrier or excipient as described herein is one or more solid, semi-solid and liquid diluents, fillers and auxiliary agents for pharmaceutical product. The pharmaceutical composition of the invention is used in the form of a dosage for unit body weight. The composition comprising the phenanthridine derivative of the invention is prepared, by using established method in pharmaceutical field and food field, into various formulations such as liquid formulations (injection, suspension, emulsion, solution, syrup, etc), solid formulations (tablet, capsule, granule, electuary, etc), spray, and aerosol. The medicament of the present invention can be administrated via injection (intravenous injection, intravenous drip, intramuscular injection, intraperitoneal injection, subcutaneous injection) and oral administration, sublingual administration, mucosal dialysis to treat hepatitis B and hepatitis C.

According to the invention, the present invention relates to a suitable pharmaceutically acceptable salt or hydrate of the compound of general formula (1) or stereoisomer thereof, wherein the pharmaceutically acceptable salt include, but is not limited to, a salt formed from the compound of general formula (1) and an inorganic acid such as hydrochloric acid, sulfuric acid, phosphoric acid, phosphorous acid, hydrobromic acid and nitric acid, and a salt formed from the compound of general formula (1) and an organic acid such as maleic acid, malic acid, fumaric acid, succinic acid, tartaric acid, citric acid, acetic acid, lactic acid, methanesulfonic acid, p-toluenesulfonic acid, palmitic acid. Some compounds of the present invention may be crystallized or recrystallized with water or various organic solvents. In this case, various solvates may be formed. The present invention includes those stoichiometric solvates and hydrates. The present invention also includes compounds containing variable amounts of water generated during the preparation by using lyophylization.

According to the invention, the stereoisomer of the compound of formula (1) of the invention means that certain compounds of the present invention may exist in a form of an optical isomer or tautomer, and all of such forms, especially the form of a pure isomer, are within the scope of the present invention. Different isomers may be separated or divided from each other by various conventional means, or some isomer may be obtained by various conventional synthetic methods or stereospecific or asymmetric synthesis methods. Since the compound of formula (1) is used for medicinal purposes, it should be understood that it is preferably provided in a pure form, for example, having a purity of at least 60%, more suitably 75%, more preferably 85%, most preferably at least 98% (% refers to the percentage by weight). The preparation method of impure compound may be used for the preparation of purer forms of the pharmaceutical composition. These impure products contain at least 1%, more suitably 5%, more preferably at least 10% of the compound of general formula (1) or pharmaceutically acceptable derivative thereof.

The pharmaceutically acceptable carrier contained in the pharmaceutical composition of the present invention includes, but is not limited to, ion exchanger, alumina, aluminum stearate, lecithin, serum protein for example human serum albumin, buffer substance such as phosphate, glycerine, sorbic, potassium sorbate, a mixture of partial glycerol ester of saturated vegetable fatty acid, water, salt or electrolyte, such as protamine sulfate, disodium hydrogen phosphate, potassium hydrogen phosphate, sodium chloride, zinc salt, colloidal silica, trisilicate magnesium, polyvinylpyrrolidone, cellulosic material, polyethylene glycol, sodium carboxymethylcellulose, polyacrylate, beeswax, wool vinegar. The content of the carrier in the pharmaceutical composition may be 1 wt % to 98 wt %, and generally the carrier account for about 80% by weight. For convenience, a local anesthetic, a preservative, a buffer and the like can be directly dissolved in the carrier.

Oral preparations such as oral tablets and capsules can contain excipients, such as binding agents, for example, syrup, arabic gum, sorbitol, tragacanth, or polyvinylpyrrolidone; fillers, for example, lactose, sucrose, corn starch, calcium phosphate, sorbitol, glycine; lubricants, for example, magnesium stearate, talc, polyethylene glycol, silica; disintegrating agents, for example potato starch; or acceptable smoothing agents, for example, sodium lauryl sulfate. The tablets may be coated by a pharmaceutically known method.

Oral liquid of the pharmaceutical composition of the invention can be prepared into suspension of oil and water, solution, emulsion, syrup or elixir, and can also be prepared into dried product, which is dissolved into water or other appropriate mediums before use. These liquid preparations can contain general additives, such as suspending agent, for example, sorbitol, cellulose methyl ether, glucose syrup, gelatin, hydroxyethyl cellulose, carboxymethyl cellulose, aluminum stearate gel, hydrogenated edible fats; emulsifying agents, for example, such as lecithin, sorbitan monooleate, arabic gum; or non-aqueous carrier (which may contain edible oils), for example, almond oil, grease like glycerin, ethylene glycol, or ethanol; preservatives, for example, methyl or propyl parahydroxybenzoates, sorbic acid. Flavoring or coloring agents can be added if needed.

Suppositories can include conventional suppository matrix, such as cocoa butter or other glycerides. For non-intestinal administration, liquid dosage form is usually made of the compound and at least one disinfected or sterile carriers. The preferred carrier is water. In accordance with selected carrier and concentration of a medicament, the compound may be dissolved into the carrier or prepared into suspending solution. When made into solution for injection, the compound is firstly dissolved in water, then filtrated for disinfection before bottled into sealed bottles or ampoules. When applied to the skin topically, the compound of the present invention can be made into proper ointment, lotion or cream, wherein the active agent is suspended or dissolved in one or more carriers. The carrier which may be used in ointment preparations include, but is not limited to, mineral oil, liquid petrolatum, white petrolatum, propylene glycol, polyoxyethylene, polyoxypropylene, emulsifying wax and water. The carrier which may be used in the lotion and the cream include, but is not limited to, mineral oil, dehydrated sorbitan monostearate, Tween 60, cetyl esters wax, hexadecene aromatic alcohol, 2-octyldodecanol, benzyl alcohol and water. According to the method of administration, the composition may contain 0.1% by weight, or more suitably 10-60% by weight of the active agent. When the composition is in unit dosage form, each unit dosage preferably contains 50 to 500 mg of active agent. Based on the method of administration and dosing frequency, a suitable treatment dose for adults is such as 100-3000 mg per day, for example 1500 mg per day.

It must be recognized that, the best dose and interval of administration of the compound of general formula (1) are determined by severity of a disease or symptom, properties of a compound and conditions such as method of administration, route of administration and site of administration as well as specific mammals to be treated. The best dose can be determined by clinicians.

BRIEF DESCRIPTION OF THE DRAWINGS

FIG. 1 shows effects of Compounds hlyc60 (10q), hlyc67 (10r), hlyc68 (11q) and hlyc69 (11r) on activity of the reporter gene TOPFlash in classical Wnt signaling pathway: After HEK293T cells are transfected with the reporter gene TOPFlash for 18 hours, conditioned mediums with a certain concentration for Wnt3a having hlyc60, hlyc67, hlyc68 and hlyc69 respectively as well as control medium having solvent control DMSO are added. After 6 hours, the cells are collected and activities of the report genes are determined.

DETAILED DESCRIPTION

The invention now will be illustrated in detail in the following examples, but those skilled in the art would understand that the following examples are merely to illustrate the invention and should not be deemed as any limitation of the scope of the invention. The specific conditions which are not indicated, are in accordance with or recommended by the manufacturer. The reagents or equipments which manufacturers are not indicated, are conventional commercially available products.

Unless otherwise stated, experimental methods, detection methods and preparation methods disclosed in the present invention are conventional techniques of organic chemistry, analytical chemistry, cell culture and recombinant DNA in the art and conventional techniques of related fields. These techniques have been completely described in the literatures, see Sambrook et al., MOLECULAR CLONING: A LABORATORY MANUAL, Second edition, Cold Spring Harbor Laboratory Press, 1989 and Third Edition, 2001; Ausubel. et al, CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, Chromatin (P. M. Wassarman and A. P. Wolffe, eds.), Academic Press, San Diego, 1999; and METHODS IN MOLECULAR BIOLOGY, Vol. 119, Chromatin Protocols (P. B. Becker, ed.) Humana Press, Totowa, 1999, etc.

Example 1: Synthesis of the Compound of General Formula (1)

(A) Experimental Conditions

ESI and high resolution mass spectrometry were determined with Finnigan MAT 90 and VG Auto Spec-3000 mass spectrometry. The melting point was determined with X-4 melting point apparatus (Gongyi Yuhua experimental equipment factory). Nuclear magnetic spectroscopy was determined with Bruker AM-400, DRX-500 and Avance III 600 nuclear resonance spectrometer, wherein deuterated chloroform and deuterated DMSO were used as solvent. Me4Si was used as internal standard. Silica gel: 60-80 mesh and 300-400 mesh (Qingdao Haiyang Chemical Co., Ltd). silica gel plate: pre-coated silica gel 60 F254 (Merck, Darmstadt, Germany). HPLC: Hypersil Gold RP-C18 Column (Thermo Fisher Scientific Inc., Waltham, Mass., USA), reagents and solvents: Aldrich-sigma Chemical Co., Acros Organics and J&KScientific.

B) Synthesis of the Compound of General Formula (1)

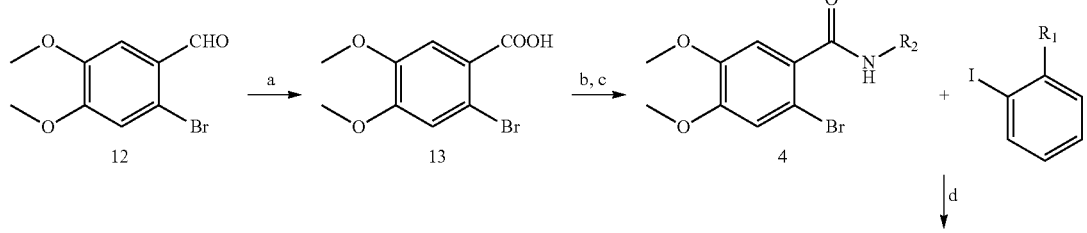

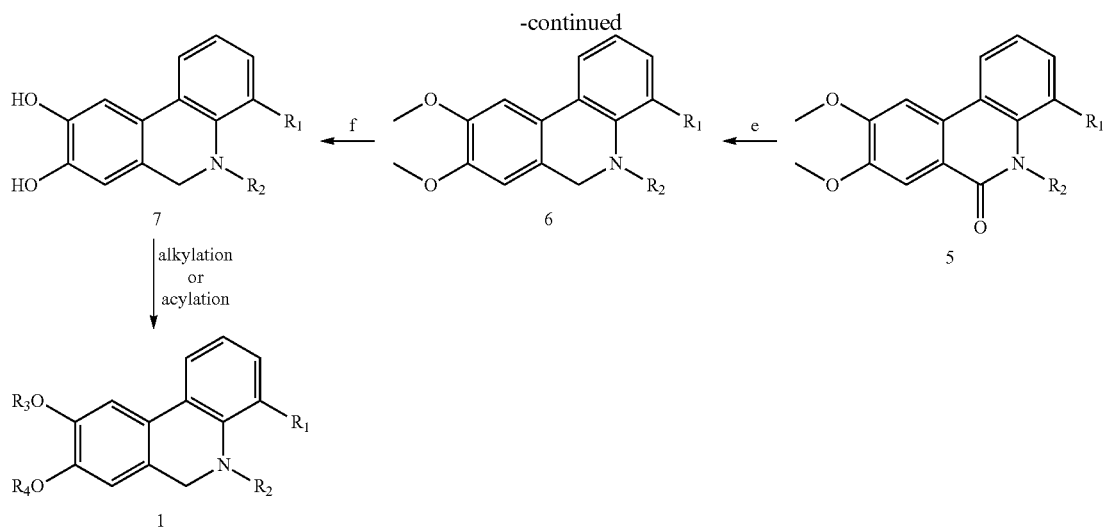

Reagents and conditions: a. NaHCO$_3$, KMnO$_4$, H$_2$O, 90° C., 3 h, 85%; b. SOCl$_2$, DMF, THF, 50° C., 2 h; c. R$_2$NH$_2$ (30%), 5° C., 1 h, 75%; d. K$_2$CO$_3$, norbomene, Pd(OAc)$_2$, TFP, MeCN, 85° C., 6 h, 75%; e. LAH, THF, −78° C., 2 h, 60%; f. BBr$_3$, CH$_2$Cl$_2$, −78° C., 4 h, 80%.

Wherein, R$_1$ was methyl, ethyl, vinyl; R$_2$ was H, methyl, ethyl; R$_3$ or R$_4$ was H, methyl, propyl, isopropyl, propenyl, n-butyl, isobutyl, tert-butyl, cyclopropylmethyl, cyclobutylmethyl, cyclohexylmethyl, benzyl, 2,3-dimethoxybenzyl; 3,5-dimethoxybenzyl, tert-butyldimethylsilyl, trimethylsilyl; acetyl, propionyl, butyryl, isobutyryl, valeryl, isovaleryl, benzoyl, p-methoxybenzoyl, 3-methoxybenzoyl, bromobenzoyl, chlorobenzoyl, 3,5-dimethoxybenzoyl, 2,3-dimethoxy-benzoyl, 3,4,5-trimethoxybenzoyl, 1-(2-aminoethyl)-1H-[1,2,3]triazol-4-methyl, 1-(2-acetylamino-ethyl)-1H-[1,2,3]triazol-4-methyl.

(C) Synthesis of the Compound of General Formula (1) from Lycorine

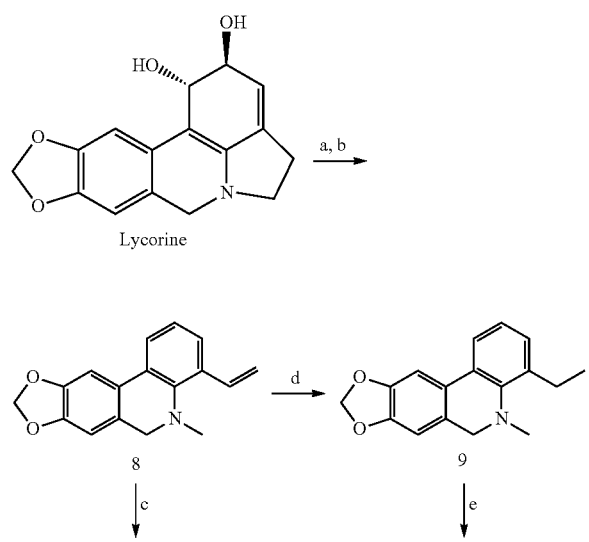

Reagents and conditions: a. CH$_3$I, r.t., 12 h; b. KTB, TBA, 90° C., 4 h, 90%; c. BBr$_3$, CH$_2$Cl$_2$, −78° C., 6 h, 65%; d. 10% Pb/C, H$_2$, 24 h, 95%; e. BBr$_3$, CH$_2$Cl$_2$, −78° C., 10 h, 72%.

Example 2: Synthesis of Specific Compounds (1) 2-bromo-4,5-dimethoxybenzoic acid (13): 2-bromo-4,5-dimethoxy-benzaldehyde (250 mg, 1 mmol), sodium hydrogen carbonate (200 mg), and potassium permanganate (500 mg) were dissolved into water (20 mL), heated with stirring for 3 hours, and then extracted with 20 ml of dichloromethane for two times, organic phases were combined, washed respectively with saturated ammonium chloride solution and saturated saline solution, dried overnight with anhydrous magnesium sulfate, filtered, and evaporated to remove excess solvent. An obtained residue was purified by silica gel column chromatography to yield a light yellow solid compound 13 (220 mg, yields: 85%).

(2) 2-bromo-4,5-dimethoxy-N-methyl-benzamide (14): compound 13 (260 mg, 1 mmol) was dissolved into THF (10 mL) followed by an addition of DMF (0.1 mL) and thionyl chloride (0.5 mL, 4 mmol). The resultant reaction solution was stirred at 50° C. for 2 hours, and then THF was removed under reduced pressure. The obtained residue was added dropwise to 30% of methylamine solution (20 ml) at 5° C., and the reaction was then left to stir for 1 hour before filtration. A filter cake was purified by column chromatography to give compound 14 (204 mg, yield: 75%).

(3) 4-ethyl-5-methyl-5H-8,9-dimethoxyphenanthridin-6-one (15): under nitrogen atmosphere, palladium acetate (3.0 mg, 0.013 mmol), TFPA (6.2 mg, 0.027 mmol), anhydrous potassium carbonate (72.3 mg, 0.52 mmol), compound 4 (0.1 mmol), and 2-ethyl-iodobenzene (0.26 mmol) were added to a round bottom flask, and anhydrous acetonitrile was added to dissolve the above mixture. An aqueous solution containing norbornene (26.9 mg, 0.286 mmol) was added, and the resultant reaction mixture was stirred for 6 hours at 85° C. then cooled to room temperature. The reaction mixture was quenched with saturated ammonium chlorine (30 mL), and extracted with ethyl acetate (3×15 ml). The organic layer was dried with anhydrous sodium sulfate, and then concentrated. The obtained residue was purified by column chromatography to give compound 15 (22.5 mg, yield: 75%).

(4) 4-ethyl-5-methyl-8,9-dimethoxy-5,6-dihydro-phenanthridine (10a): compound 15 (30 mg, 0.1 mmol) was dissolved into THF (5 mL). LAH (20 mg) was added at −78° C., the reaction mixture was stirred for 2 hours then quenched with water. The resultant mixture was extracted with ethyl ether (20 mL) twice, the organic phase was washed with saturated saline solution and concentrated. The obtained residue was purified by column chromatography to give compound 10a (21 mg, yield: 75%).

(5) 4-ethyl-5-methyl-5,6-dihydro-phenanthridine-8,9-diol (10): compound 10a (29 mg, 0.1 mmol) was dissolved in dichloromethane, the reaction solution was cooled to −78° C. then added dropwise with BBr$_3$ (100 μL, 0.2 mmol). The resultant reaction liquid was stirred for 4 hours then diluted with saturated sodium hydrogen carbonate solution (10 mL), and extracted twice with dichloromethane (15 mL). The organic phase was concentrated and purified by silica gel column chromatography to give compound 10 (120 mg, yield: 80%).

(6) 5-methyl-4-vinyl-5,6-dihydro-[1,3]dioxolo[4,5-j]phenanthridine (8): lycorine (300 mg, 1 mmol) was dissolved in DMF (10 mL), methyl iodide (400 μL, 2 mmol) was added then stirred for 12 hours at room temperature. DMF was removed under reduced pressure, then t-butanol (TBA, 10 mL) and potassium tert-butoxide (PTB, 1.1 g, 10 mmol) were added. The reaction liquid was heated to reflux and reacted for 4 h, then quenched with saturated ammonium chloride solution. The resultant mixture was extracted twice with ethyl ether (20 mL). The organic phase was concentrated and the residue was purified by column chromatography to give compound 8 (240 mg, yield: 90%).

(7) 4-ethyl-5-methyl-5,6-dihydro-[1,3]dioxolo[4,5-j]phenanthridine (9): compound 8 (27 mg, 0.1 mmol) was dissolved in dichloromethane (5 mL), 10% of Pb/C (30 mg) was added and stirred in a hydrogen atmosphere for 24 h then filtered. The filtrate was concentrated and the residue was purified by column chromatography to give compound 9 (25 mg, yield: 95%).

(8) 4-ethyl-5-methyl-5,6-dihydro-phenanthridine-8,9-diol (10): compound 9 (55 mg, 0.2 mmol) was dissolved in methylene chloride (10 ml), the reaction solution was cooled to −78° C., then BBr$_3$ (200 μL, 0.4 mmol) was added dropwise. The reaction liquid was stirred for 10 hours, then diluted with saturated sodium hydrogen carbonate solution (50 mL). The resultant mixture was extracted twice with dichloromethane (25 mL). The organic phase was concentrated and purified by silica gel chromatography to give compound 10 (35.7 mg, yield: 72%).

(9) 4-ethenyl-5-methyl-5,6-dihydrophenanthridine-8,9-diol (11): compound 8 (52 mg, 0.2 mmol) was dissolved in methylene chloride (10 ml), the reaction solution was cooled to −78° C. and BBr$_3$ (200 μL, 0.4 mmol) was added dropwise. The resultant reaction liquid was stirred for 10 hours then diluted with saturated sodium hydrogen carbonate solution (50 mL). The resultant mixture was extracted twice with dichloromethane (25 mL). The organic phase was concentrated and purified by silica gel column chromatography to give compound 11 (33.2 mg, yield: 65%).

(10) Alkylation of compounds 10 and 11: compounds 10 or 11 (0.1 mmol) was dissolved into dried THF (10 mL), NaH (50 mg, 2 mmol) and haloalkane (1 mmol) were added. The reaction solution was stirred at room temperature for 24 hours, then quenched with water (50 mL). The resultant reaction liquid was concentrated to remove excess THF. The resultant mixture was extracted twice with dichloromethane (30 mL). The organic phase was washed with saturated sodium hydrogen carbonate solution and saturated saline solution then concentrated. The obtained residue was purified by column chromatography to give compound 10 a-h or 11 a-g.

(11) Acylation of compounds 10 and 11: compounds 10 or 11 (0.1 mmol) was added to a solution of pyridine (3 mL), anhydride or acyl chloride (0.5 mmol), and DMAP (30 mg), then stirred at room temperature for 20 hours. The reaction liquid was poured into an ice-water mixture (50 mL) after the reaction and stirred vigorously. The resultant mixture was extracted twice with ethyl acetate (30 mL). The organic phase was washed with saturated saline solution and concentrated. The obtained residue was purified by column chromatography to give compound 10 j-p or 11 h-n.

(12) Preparation of compound 16: 2-Bromoethylamine hydrobromide (500 mg, 2.44 mmol) and sodium azide (475.9 mg, 7.32 mmol) were dissolved in H$_2$O (2 mL) and stirred at 75° C. for 21 h then cooled to 0° C., and potassium hydroxide (KOH) (800 mg) and Et$_2$O (2 mL) were added. The aqueous layer was extracted twice using ethyl ether (2×10 ml), and the organic layer was washed with saturated saline solution and dried with anhydrous magnesium sulfate. The volatile solvents were removed under reduced pressure. The obtained residue was purified by silica gel column chromatography (chloroform/methanol 20:1, R$_f$=0.21) to give compound 16 as a yellow liquid (171 mg, 1.99 mmol, yield: 82%).

(13) Preparation of compound 10q: compound 10d (33.1 mg, 0.1 mmol) and compound 16 (30.1 mg, 0.4 mmol) were dissolved in tBuOH (5 mL), an aqueous solution of sodium ascorbate (19.8 mg, 0.1 mmol) and copper sulfate (1.8 mg, 0.01) in H$_2$O (2 ml) were added in the above tBuOH solution and stirred at 50° C. for 12 hours. The solvent was removed under reduced pressure. The obtained residue was purified by silica gel chromatography column (chloroform/methanol 25:1, R$_f$=0.23) to give compound 10q as yellow solid (57.3 mg, yield: 60%). m.p. 196-197° C.

(14) Preparation of compound 10r: compound 10q (50 mg, 0.1 mmol) was dissolved in pyridine (5 mL) at 0° C., and acetic anhydride (100 μl) was added then stirred at room temperature for 12 hours. The reaction solution was adjusted to pH 8-9 with saturated NaHCO$_3$ solution and the organic solvent was removed under reduced pressure. The obtained residue was purified by silica gel chromatography column (chloroform/methanol 9:1, R$_f$=0.34) to give compound 10r as yellow solid (46.3 mg, yield: 62%).

(15) Preparation of compound 11q: compound 11d (33.1 mg, 0.1 mmol) and compound 16 (30.1 mg, 0.4 mmol) were dissolve in tBuOH (5 mL), an aqueous solution (2 ml) of sodium ascorbate (19.8 mg, 0.1 mmol) and copper sulfate (1.8 mg, 0.01) in water (2 ml) was added in to the above tBuOH solution and stirred at 50° C. for 12 hours. The solvent was removed under reduced pressure. The obtained residue was purified by silica gel column chromatography (chloroform/methanol 25:1, R$_1$=0.46) to give compound 11q as yellow solid (56.1 mg, yield: 57%).

(16) Preparation of compound 11r: compound 11q (51 mg, 0.1 mmol) was dissolved in pyridine (5 mL) at 0° C., and acetic anhydride (100 μl) was added and stirred at room temperature for 12 hours. The reaction solution was adjusted to pH 8-9 with saturated NaHCO$_3$ solution, the organic solvent was removed under reduced pressure. The obtained residue was purified by silica gel column chromatography (chloroform/methanol 12:1, R$_f$=0.44) to give compound 11r as yellow solid (48.1 mg, yield: 61%).

A preparation method of 10q, 10r, 11q, 11r were shown as follow:

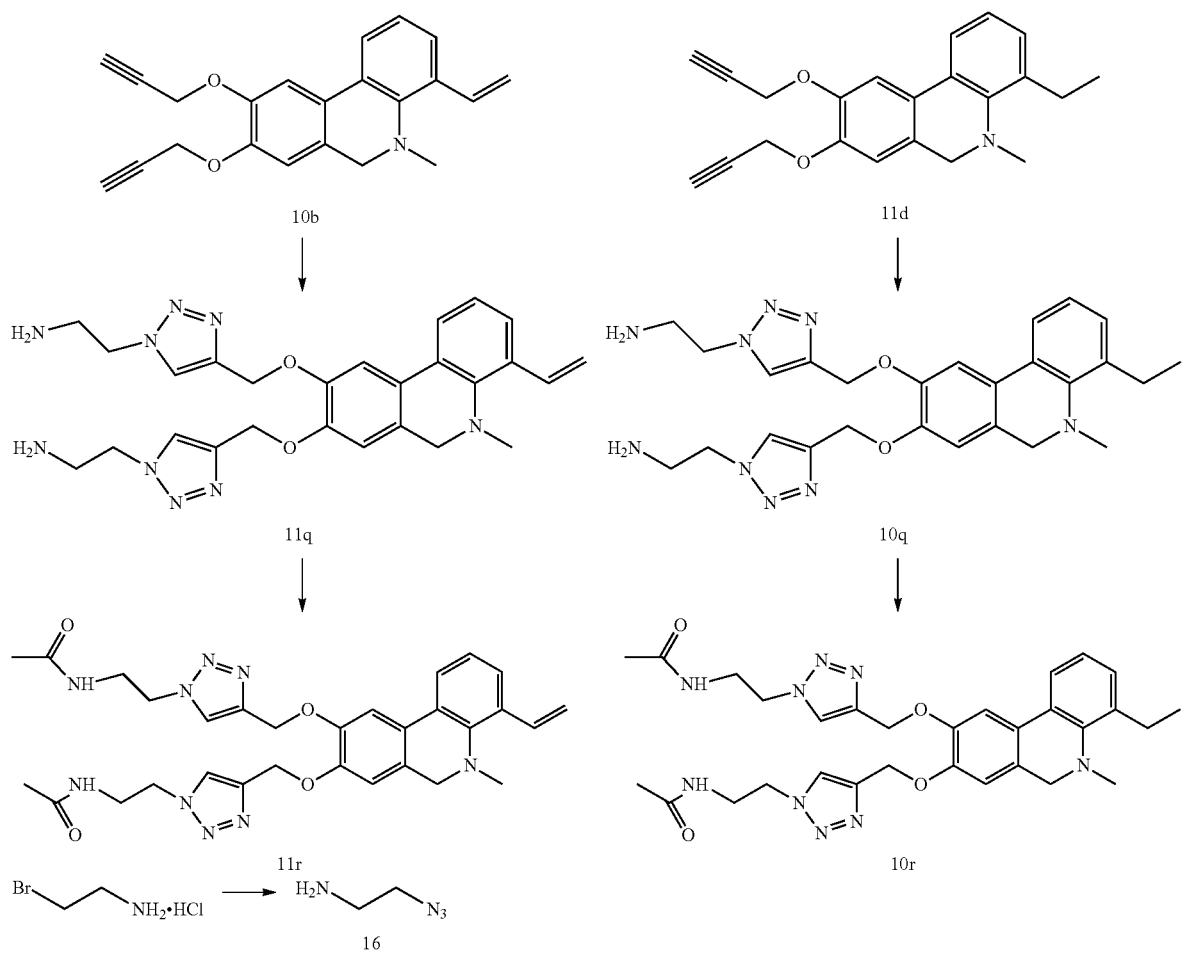

Structure formulas of the above compounds were:

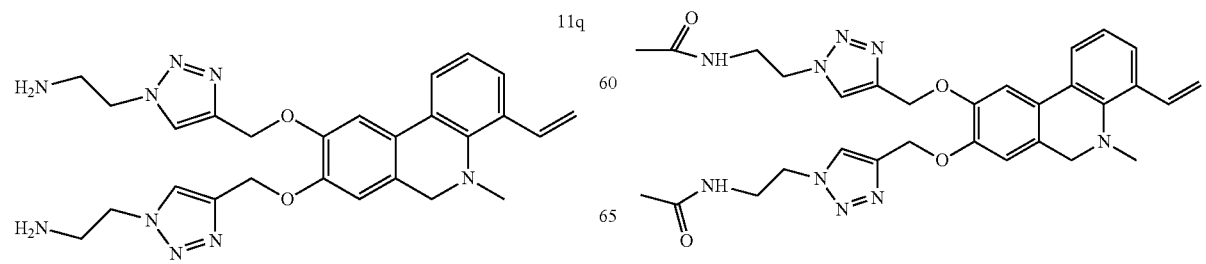

| | 10r |
|---|---|
| | 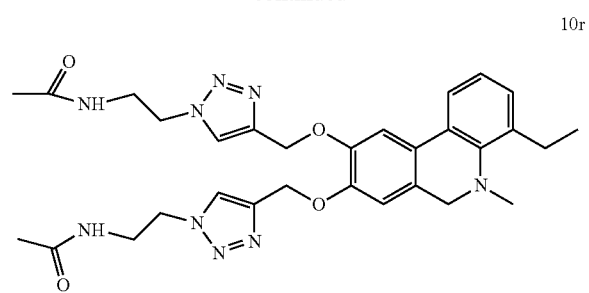 |
| compound | R |
|---|---|
| 10 | H |
| 10a | —CH₃ |
| 10b | —CH₂CH₃ |
| 10c | (but-3-enyl) |
| 10d | (propargyl) |
| 10e | (cyclobutylmethyl) |
| 10f | (cyclohexylmethyl) |
| 10g | (benzyl) |
| 10h | (2,3-dimethoxybenzyl) |
| 10j | Ac |
| 10k | 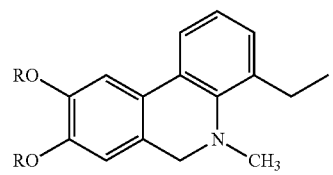 |
| 10l | (isobutyryl) |
| 10m | (butyryl) |
| 10n | (isovaleryl) |
| 10o | (benzoyl) |
| 10p | (4-bromobenzoyl) |
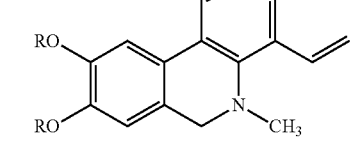
| compound | R |
|---|---|
| 11a | (but-3-enyl) |
| 11b | (propargyl) |
| 11c | (cyclobutylmethyl) |
| 11d | (cyclohexylmethyl) |
| 11e | (benzyl) |

| | |
|---|---|
| 11f | 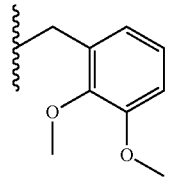 [SMILES: *Cc1cccc(OC)c1OC] |
| 11g | 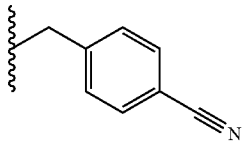 [SMILES: *Cc1ccc(C#N)cc1] |
| 11h | Ac |
| 11i | 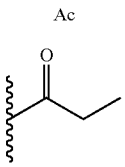 |
| 11j | 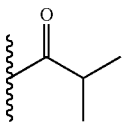 [SMILES: *C(=O)C(C)C] |
| 11k | 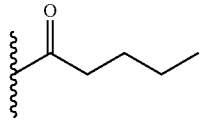 |
| 11l | 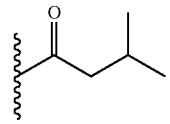 [SMILES: *C(=O)CC(C)C] |
| 11m | 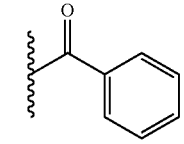 [SMILES: *C(=O)c1ccccc1] |
| 11n | 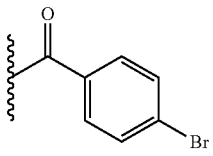 [SMILES: *C(=O)c1ccc(Br)cc1] |

Spectral Data of Compounds:

2-bromo-4,5-dimethoxybenzoic acid (13): $^1$H NMR (500 MHz, CDCl$_3$) δ 7.54 (s, 1H), 7.52 (s, 1H), 3.87 (s, 3H), 3.81 (s, 3H); $^{13}$C NMR (125 MHz, CDCl$_3$) δ 169.87, 153.3, 152.14, 121.85, 116.73, 115.31, 111.64, 56.81; ESI$^+$ MS m/z 261 [M+H]$^+$.

2-bromo-4,5-dimethoxy-N-methyl-benzamide (14): $^1$H NMR (400 MHz, CDCl$_3$) δ 7.46 (s, 1H), 7.33 (s, 1H), 6.63 (s, 1H), 3.87 (s, 1H), 3.85 (s, 3H), 2.79 (s, 3H); 13C NMR (100 MHz, CDCl$_3$) δ 169.31, 152.32, 151.16, 131.95, 116.69, 116.31, 112.86, 56.81, 56.78, 26.33; ESI$^+$MS m/z 274 [M+H]+.

4-ethyl-5-methyl-5H-8,9-dimethoxyphenanthridin-6-one (15): $^1$H NMR δ 8.21 (d, J=7.6 Hz, 1H), 7.71 (s, 1H), 7.60 (s, 1H), 7.32 (d, J=7.4 Hz, 1H), 7.29-7.25 (m, 1H), 3.92 (s, 3H), 3.89 (s, 3H), 3.76 (s, 3H), 3.01-3.03 (m, 2H), 1.25 (t, J=8.1 Hz, 3H); $^{13}$C NMR: δ166.1, 139.4, 134.5, 132.5, 132.1, 131.3, 128.7, 127.5, 125.1, 129.6, 122.2, 121.1, 121.0, 58.3, 58.1, 38.6, 28.1, 15.5; HREIMS m/z 297.1361 [M]$^+$ (calcd for C$_{18}$H$_{19}$NO$_3$, 297.1365).

5-methyl-4-vinyl-5,6-dihydro-[1,3]dioxolo[4,5-j]phenanthridine (8): m.p. 152-154° C.; $^1$H NMR (400 MHz, CDCl$_3$) δ: 7.58 (d, J=7.7 Hz, 1H), 7.47 (d, J=7.7 Hz, 1H), 7.26 (dt, J=10.7, 7.1 Hz, 2H), 7.16 (t, J=7.7 Hz, 1H), 6.72 (s, 1H), 5.99 (s, 2H), 5.75 (d, J=17.8 Hz, 1H), 5.32 (d, J=11.1 Hz, 1H), 4.03 (s, 2H), 2.51 (s, 3H); $^{13}$C NMR (100 MHz, CDCl$_3$) δ: 147.4 (C), 145.1 (C), 133.4 (CH), 133.2 (C), 129.2 (C), 126.4 (C), 125.8 (C), 124.9 (CH), 124.3 (CH), 122.7 (CH), 114.3 (CH$_2$), 107.1 (CH), 103.6 (CH), 100.9 (CH$_2$), 54.8 (CH$_2$), 41.5 (CH), ESI$^+$ MS m/z: 266 [M+H]$^+$.

4-ethyl-5-methyl-5,6-dihydro-[1,3]dioxolo[4,5-j]phenanthridine (9): m.p. 179-180° C.; $^1$H NMR (400 MHz, CDCl$_3$) δ: 7.51 (t, J=8.4 Hz, 1H), 7.28 (d, J=6.4 Hz, 2H), 7.20 (t, J=7.9 Hz, 2H), 6.75 (s, 1H), 6.01 (s, 1H), 4.01 (s, 2H), 2.83 (q, J=7.5 Hz, 2H), 2.50 (s, 3H), 1.32 (dd, J=15.7, 8.2 Hz, 3H); $^{13}$C NMR (100 MHz, CDCl$_3$) δ: 147.3 (C), 147.1 (C), 145.4 (C), 139.4 (C), 129.3 (C), 127.7 (CH), 126.6 (C), 126.3 (C), 124.6 (CH), 121.0 (CH), 107.2 (CH), 103.7 (CH), 100.9 (CH$_2$), 55.2 (CH$_2$), 41.02 (CH), 23.1 (CH$_2$), 14.8 (CH$_3$), HREIMS m/z 217.1261 [M]$^+$ (calcd for C$_{17}$H$_{17}$NO$_2$, 267.1259).

4-ethyl-5-methyl-5,6-dihydro-phenanthridine-8,9-diol (10): $^1$H NMR (400 MHz, CDCl$_3$) δ: 7.46 (d, J=7.1 Hz, 1H), 7.27 (d, J=2.7 Hz, 1H), 7.15 (dt, J=15.0, 7.5 Hz, 1H), 6.75 (s, 1H), 3.96 (s, 2H), 2.82-2.76 (m, 2H), 2.47 (s, 3H), 1.28 (dd, J=14.7, 7.1 Hz, 3H); $^{13}$C NMR (100 MHz, CDCl$_3$) δ: 143.8 (C), 143.0 (C), 139.4 (C), 128.8 (C), 127.6 (CH), 125.1 (C), 124.7 (CH), 120.9 (CH), 113.8 (CH), 110.4 (CH), 54.6 (CH$_2$), 41.2 (CH), 23.1 (CH$_2$), 14.8 (C H$_3$). HREIMS m/z 255.1250 [M]$^+$ (calcd for C$_{16}$H$_{17}$NO$_2$, 255.1259).

4-ethyl-5-methyl-8,9-dimethoxy-5,6-dihydro-phenanthridine (10a): $^1$HNMR (600 MHz, CDCl$_3$) δ 7.93 (d, J=7.1 Hz, 1H), 7.83 (s, 1H), 7.51 (s, 1H), 7.30 (d, J=6.9 Hz, 1H), 7.19 (m, 1H), 4.06 (s, 2H), 4.02 (s, 3H), 3.98 (s, 3H), 3.73 (s, 3H), 2.96 (q, J=7.4 Hz, 2H), 1.23 (t, J=7.5 Hz, 3H); $^{13}$C NMR (151 MHz, CDCl$_3$) δ 153.43 (C), 146.53 (C), 140.53 (C), 138.79 (C), 132.97 (C), 131.32 (CH), 130.02 (C), 129.03 (C), 123.15 (CH), 120.53 (CH), 108.86 (CH), 103.06 (CH), 60.28 (CH$_2$), 56.47 (CH$_3$), 56.35 (CH$_3$), 38.89 (CH$_3$), 28.48 (CH$_2$), 15.80 (CH$_3$). HREIMS m/z 283.1567 [M]$^+$ (calcd for C$_{18}$H$_{21}$NO$_2$, 283.1572).

4-ethyl-5-methyl-8,9-diethyoxy-5,6-dihydro-phenanthridine (10b): $^1$H NMR (600 MHz, CDCl$_3$) δ 7.57 (d, J=7.8 Hz, 1H), 7.47 (t, J=7.8 Hz, 1H), 7.41 (s, 1H), 7.33 (d, J=7.9 Hz, 1H), 6.83 (s, 1H), 4.45 (s, 2H), 3.46 (q, J=7.1 Hz, 2H), 3.39 (q, J=7.1 Hz, 2H), 2.93 (s, 3H), 2.35-2.31 (m, 2H), 1.49-1.43 (m, 3H); $^{13}$C NMR (151 MHz, CDCl$_3$) δ 157.33 (C), 148.42 (C), 141.38 (C), 139.71 (C), 133.34 (C), 132.12 (CH), 130.83 (C), 129.13 (C), 124.05 (CH), 121.13 (CH), 107.56 (CH), 106.16 (CH), 58.28 (CH$_2$), 58.17 (CH$_2$), 58.03 (CH$_2$), 38.89 (CH$_3$), 28.48 (CH$_2$), 16.75 (CH$_3$), 16.63 (CH$_3$), 15.80 (CH$_3$). HREIMS m/z 311.1874 [M]$^+$ (calcd for C$_{20}$H$_{25}$NO$_2$, 311.1885).

4-ethyl-5-methyl-8,9-diallyloxy-5,6-dihydro-phenanthridine (10c): $^1$H NMR (600 MHz, CDCl$_3$) δ 7.74 (d, J=3.1 Hz, 1H), 7.61-7.58 (m, 2H), 7.52-7.42 (m, 2H), 7.34 (dd, J=13.3, 6.1 Hz, 3H), 6.89 (s, 1H), 5.99-6.03 (m, 2H), 5.47-5.26 (m, 4H), 3.92 (s, 2H), 3.45 (s, 3H), 2.92 (q, J=7.5 Hz, 2H), 1.38 (t, J=7.5 Hz, 3H); $^{13}$C NMR (101 MHz, CDCl$_3$) δ: 148.5 (C), 147.8 (C), 145.5 (C), 139.4 (C), 133.6 (C), 133.6 (CH), 129.1 (C), 127.6 (CH), 125.8 (C), 125.3 (C), 124.5 (CH), 120.8 (CH), 117.6 (CH$_2$), 117.6 (CH$_2$), 112.4 (CH$_2$), 109.7

(CH$_2$), 70.4 (CH$_2$), 69.9 (CH$_2$), 54.8 (CH$_2$), 41.2 (CH$_3$), 23.1 (CH$_2$), 14.8 (CH$_3$). HREIMS m/z 335.1894 [M]$^+$ (calcd for C$_{22}$H$_{25}$NO$_2$, 335.1885).

4-ethyl-5-methyl-8,9-diprop-2-ynyloxy-5,6-dihydro-phenanthridine (10d): $^1$H NMR (400 MHz, CDCl$_3$) δ: 7.55 (dd, J=7.0, 2.1 Hz, 1H), 7.47 (s, 1H), 6.92 (s, 1H), 4.82 (dd, J=10.9, 2.4 Hz, 3H), 4.03 (s, 2H), 2.85-2.77 (m, 2H), 2.59-2.54 (m, 1H), 2.51-2.47 (m, 3H), 1.30 (q, J=7.5 Hz, 3H); $^{13}$C NMR (100 MHz, CDCl$_3$) δ: 147.4 (C), 146.8 (C), 145.6 (C), 139.5 (C), 128.9 (C), 127.9 (CH), 126.8 (C), 126.3 (C), 124.6 (CH), 121.0 (CH), 113.1 (CH), 110.5 (CH), 78.6 (C), 78.4 (C), 75.9 (C), 75.9 (C), 57.2 (CH$_2$), 56.9 (CH$_2$), 54.8 (CH$_2$), 41.31 (CH), 23.1 (CH$_2$), 14.8 (CH$_3$); HREIMS m/z 331.1579 [M]$^+$ (calcd for C$_{22}$H$_{21}$NO$_2$, 331.1572).

4-ethyl-5-methyl-8,9-bis-cyclohexylmethoxy-5,6-di-hydro-phenanthridine (10e): $^1$H NMR (400 MHz, CDCl$_3$) δ: 7.53 (d, J=7.1 Hz, 1H), 7.32 (d, J=2.7 Hz, 1H), 7.18-7.11 (m, 2H), 6.92 (s, 1H), 4.28 (d, J=8.3 Hz, 2H), 4.25 (d, J=8.3 Hz, 2H), 4.10 (s, 2H), 2.68-2.62 (m, 2H), 2.94 (s, 3H), 2.64-2.52 (m, 2H), 2.49-2.32 (m, 2H), 2.07-1.58 (m, 8H), 1.32 (t, 3H), 1.39-1.36 (m, 3H); $^{13}$C NMR (100 MHz, CDCl$_3$) δ: 144.6 (C), 143.8 (C), 138.5 (C), 128.2 (C), 127.1 (CH), 124.8 (C), 125.1 (CH), 124.3 (C), 121.2 (CH), 120.2 (C), 114.3 (CH), 111.0 (CH), 69.73 (CH$_2$), 69.70 (CH$_2$), 57.6 (CH$_2$), 41.2 (CH$_3$), 32.58 (CH), 32.54 (CH), 25.28 (2CH$_2$), 25.24 (2CH$_2$), 24.3 (CH$_2$), 18.78 (CH$_2$), 18.74 (CH$_2$), 14.8 (CH$_3$); HREIMS m/z 391.2521 [M]$^+$ (calcd for C$_{26}$H$_{33}$NO$_2$, 391.2511).

4-ethyl-5-methyl-8,9-bis-cyclohexylmethoxy-5,6-di-hydro-phenanthridine (10f): $^1$H NMR (500 MHz, CDCl$_3$) δ: 7.58 (d, J=7.1 Hz, 1H), 7.24-7.07 (m, 3H), 7.01 (s, 1H), 4.12 (s, 2H), 4.09-3.77 (m, 4H), 3.05 (s, 3H), 2.56-2.47 (m, 2H), 1.94-1.44 (m, 12H), 1.43-1.22 (m, 4H), 1.22-0.84 (m, 9H); $^{13}$C NMR (125 MHz, CDCl$_3$) δ: 146.8 (C), 144.2 (C), 138.3 (C), 129.4 (C), 126.9 (CH), 125.3 (C), 124.8 (CH), 124.1 (C), 120.9 (CH), 119.5 (C), 113.7 (CH), 110.3 (CH), 71.6 (CH$_2$), 71.5 (CH$_2$), 58.7 (CH$_2$), 40.6 (CH$_3$), 33.7 (CH), 33.6 (CH), 28.5 (2CH$_2$), 28.4 (2CH$_2$), 26.2 (CH$_2$), 25.9 (CH$_2$), 25.8 (CH$_2$), 24.3 (2CH$_2$), 24.2 (2CH$_2$), 13.7 (CH$_3$); HREIMS m/z 447.3142 [M]$^+$ (calcd for C$_{30}$H$_{41}$NO$_2$, 447.3137).

4-ethyl-5-methyl-8,9-dibenzyloxy-5,6-dihydro-phenan-thridine (10g): $^1$H NMR (400 MHz, CDCl$_3$) δ 7.43-7.37 (m, 6H), 7.32-7.29 (m, 5H), 7.19 (s, 1H), 7.09-7.07 (m, 3H), 6.75 (s, 1H), 5.15 (s, 2H), 5.12 (s, 2H), 3.90 (s, 2H), 2.72 (q, J=7.5 Hz, 2H), 2.38 (s, 3H), 1.22 (t, J=7.5 Hz, 3H); $^{13}$C NMR (100 MHz, CDCl$_3$) δ 147.24 (C), 143.71 (C), 129.09 (C), 128.52 (C), 128.47 (2CH), 128.36 (C), 127.81 (2CH), 127.67 (CH), 127.44 (2CH), 127.38 (C), 127.34 (2CH), 125.82 (CH), 125.74 (CH), 126.32 (C), 124.57 (CH), 123.12 (C), 123.08 (C), 120.91 (CH), 113.32 (CH), 110.84 (CH), 71.89 (CH$_2$), 71.32 (CH$_2$), 54.83 (CH$_2$), 41.30 (CH$_3$), 23.13 (CH$_2$), 14.85 (CH$_3$). HREIMS m/z 435.2194 [M]$^+$ (calcd for C$_{30}$H$_{29}$NO$_2$, 435.2198).

4-ethyl-5-methyl-8,9-di(2,3-dimethoxy)benzyloxy-5,6-dihydro-phenanthridine (10h): $^1$H NMR (400 MHz, CDCl$_3$) δ 7.38 (d, J=10.6 Hz, 1H), 7.24-7.09 (m, 3H), 7.11-6.98 (m, 3H), 7.03-6.84 (m, 4H), 5.23 (s, 2H), 5.20 (s, 2H), 4.70 (s, 2H), 3.90 (s, 3H), 3.89 (s, 3H), 3.88 (s, 3H), 3.87 (s, 3H), 3.82 (s, 3H), 2.60-2.40 (m, 3H), 1.28 (d, J=18.8 Hz, 3H). $^{13}$C NMR (101 MHz, CDCl$_3$) δ152.49 (C), 146.87 (C), 146.83 (C), 145.92 (C), 145.86 (C), 144.67 (C), 142.77 (C), 140.14 (C), 136.26 (CH), 135.89 (C), 134.52 (C), 134.45 (C), 133.64 (CH), 124.20 (CH), 124.09 (CH), 121.03 (CH), 121.01 (CH), 120.97 (CH), 118.60 (CH), 113.66 (CH), 112.94 (CH), 112.92 (CH), 112.13 (CH), 112.00 (CH), 66.48 (CH$_2$), 66.30 (CH$_2$), 61.60 (CH$_3$), 61.10 (CH$_3$), 60.87 (CH$_3$), 60.84 (CH$_3$), 55.76 (CH$_2$), 39.67 (CH$_3$), 26.78 (CH$_2$), 14.13 (CH$_3$). HREIMS m/z 555.2107 [M]$^+$ (calcd for C$_{34}$H$_{37}$NO$_6$, 555.2621).

4-ethyl-5-methyl-8,9-diacetoxy-5,6-dihydro-phenanthri-dine (10j): $^1$H NMR (400 MHz, CDCl$_3$) δ: 7.49 (d, J=7.1 Hz, 1H), 7.23 (s, 1H), 7.16 (m, 1H), 7.14 (m, 1H), 6.71 (s, 1H), 3.98 (s, 2H), 2.79 (q, J=7.5 Hz, 2H), 2.46 (s, 3H), 2.44 (s, 3H), 2.38 (s, 3H), 1.29 (m, 3H); $^{13}$C NMR (100 MHz, CDCl$_3$) δ: 173.18 (C), 173.09 (C), 143.82 (C), 143.02 (C), 139.43 (C), 128.81 (C), 127.63 (CH), 125.17 (C), 124.72 (CH), 120.95 (CH), 119.23 (C), 113.86 (CH), 111.72 (C), 110.41 (CH), 54.63 (CH$_2$), 35.21 (CH$_3$), 28.52 (CH$_2$), 23.23 (CH$_3$), 23.16;' (CH$_3$), 14.8 (CH$_3$); HREIMS m/z 339.1480 [M]$^+$ (calcd for C$_{20}$H$_{21}$NO$_4$, 339.1471).

4-ethyl-5-methyl-8,9-dipropionyloxy-5,6-dihydro-phenanthridine (10k): $^1$H NMR (600 MHz, CDCl$_3$) δ 7.71-7.58 (m, 2H), 7.47 (s, 1H), 7.38 (s, 1H), 7.21 (s, 1H), 4.52 (s, 2H), 2.93 (s, 3H), 2.68 (q, J=7.5, 6.5 Hz, 2H), 2.65-2.55 (m, 4H), 1.34-1.17 (m, 9H). $^{13}$C NMR (151 MHz, CDCl$_3$) δ 172.10 (C), 171.87 (C), 159.48 (C), 142.76 (C), 137.03 (C), 133.96 (C), 132.04 (CH), 131.18 (C), 128.78 (CH), 124.52 (CH), 123.96 (CH), 121.46 (C), 117.02 (C), 112.95 (CH), 59.64 (CH$_2$), 41.18 (CH$_3$), 26.16 (CH$_2$), 26.14 (CH$_2$), 23.92 (CH$_2$), 19.68 (CH$_3$), 19.62 (CH$_3$), 14.78 (CH$_3$); HREIMS m/z 367.1775 [M]$^+$ (calcd for C$_{22}$H$_{25}$NO$_4$, 367.1784).

4-ethyl-5-methyl-5H-8,9-diisobutyryloxyphenanthridin (10l): $^1$H NMR (600 MHz, CDCl$_3$) δ 7.74 (s, 1H), 7.52-7.49 (m, 1H), 7.37-7.32 (m, 2H), 7.06 (s, 1H), 4.28 (s, 2H), 3.01 (s, 3H), 2.88-2.79 (m, 2H), 2.53-2.48 (m, 2H), 1.46-1.42 (m, 3H), 1.17-1.11 (m, 12H); $^{13}$C NMR (151 MHz, CDCl$_3$) δ 171.46 (C), 171.39 (C), 151.33 (C), 142.03 (C), 138.17 (C), 133.98 (C), 131.11 (CH), 131.25 (C), 129.86 (CH), 124.45 (CH), 123.77 (CH), 121.24 (C), 115.87 (C), 112.9 (CH), 42.72 (CH$_2$), 41.67 (CH$_3$), 33.76 (CH), 33.83 (CH), 26.92 (CH$_2$), 21.53 (2CH$_3$), 21.51 (2CH$_3$), 14.87 (CH$_3$). HREIMS m/z 395.2091 [M]$^+$ (calcd for C$_{24}$H$_{29}$NO$_4$, 395.2097).

4-ethyl-5-methyl-8,9-divaleryoxy-5,6-dihydro-phenan-thridine (10m): $^1$H NMR (600 MHz, CDCl$_3$) δ 7.80 (s, 1H), 7.60-7.57 (m, 1H), 7.51-7.46 (m, 1H), 7.28-7.23 (m, 2H), 4.18 (s, 2H), 2.87-2.79 (m, 4H), 2.57-2.52 (m, 2H), 2.98 (s, 3H), 1.82-1.76 (m, 4H), 1.64-1.58 (m, 4H), 1.43-1.40 (m, 3H), 1.08-0.98 (m, 6H); $^{13}$C NMR (151 MHz, CDCl$_3$) δ 172.10 (C), 172.08 (C), 151.55 (C), 142.23 (C), 138.34 (C), 133.96 (C), 132.01 (CH), 130.21 (C), 128.76 (CH), 124.35 (CH), 123.91 (CH), 121.27 (C), 115.67 (C), 113.79 (CH), 62.18 (CH$_2$), 43.14 (CH$_2$), 42.14 (CH$_3$), 33.77 (CH$_2$), 33.69 (CH$_2$), 26.86 (CH$_2$), 26.80 (CH$_2$), 21.14 (CH$_2$), 21.11 (CH$_2$), 17.65 (CH$_3$), 17.63 (CH$_3$), 15.35 (CH$_3$); HREIMS m/z 423.2407 [M]$^+$ (calcd for C$_{26}$H$_{33}$NO$_4$, 423.2410).

4-ethyl-5-methyl-8,9-diisovaleroxy-5,6-dihydro-phenan-thridine (10n): $^1$H NMR (600 MHz, CDCl$_3$) δ 7.78 (s, 1H), 7.54-7.50 (m, 1H), 7.43-7.40 (m, 1H), 7.39-7.36 (m, 1H), 7.10 (s, 1H), 5.16 (s, 2H), 2.94-2.90 (m, 2H), 2.93 (s, 3H), 2.51 (d, J=8.1, 2H), 2.48 (d, J=8.1, 2H), 2.35-2.19 (m, 2H), 1.40 (t, J=7.4, 2.0 Hz, 3H), 1.12-1.05 (m, 12H); $^{13}$C NMR (151 MHz, CDCl$_3$) δ 171.00 (C), 170.77 (C), 150.45 (C), 141.74 (C), 137.97 (C), 134.13 (C), 131.29 (CH), 130.74 (C), 129.34 (CH), 123.78 (CH), 123.30 (CH), 120.81 (C), 116.59 (C), 113.51 (CH), 55.94 (CH$_2$), 55.56 (CH$_2$), 43.14 (CH$_2$), 42.09 (CH$_3$), 29.92 (CH$_2$), 26.16 (CH), 26.14 (CH), 22.65 (4CH$_3$), 15.35 (CH$_3$). HREIMS m/z 423.2419 [M]$^+$ (calcd for C$_{26}$H$_{33}$NO$_4$, 423.2410).

4-ethyl-5-methyl-8,9-dibenzoyloxy-5,6-dihydro-phenan-thridine (10o): $^1$H NMR (600 MHz, CDCl$_3$) δ 8.09-8.02 (m, 5H), 7.87 (d, J=18.8 Hz, 1H), 7.68 (s, 1H), 7.56 (t, J=7.1 Hz, 3H), 7.44-7.41 (m, 2H), 7.41 (t, J=7.8 Hz, 5H), 4.34 (q, J=5.9 Hz, 2H), 3.05 (s, 3H), 1.39 (t, J=6.1 Hz, 3H); $^{13}$C NMR (151 MHz, CDCl$_3$) δ 170.88 (C), 170.62 (C), 151.38 (C), 144.62 (C), 133.45 (C), 134.38 (C), 130.14 (C), 130.19 (C), 130.02 (CH), 129.42 (2CH), 129.38 (2CH), 129.14 (C), 128.92 (CH), 126.20 (2CH), 126.18 (2CH), 124.72 (C), 124.63 (C), 123.68 (CH), 122.84 (CH), 120.81 (C), 114.38 (C), 113.72 (CH), 59.68 (CH$_2$), 42.13 (CH$_3$), 25.72 (CH$_2$), 14.96 (CH$_3$). HREIMS m/z 463.1778 [M]$^+$ (calcd for C$_{30}$H$_{25}$NO$_4$, 463.1784).

4-ethyl-5-methyl-8,9-di(4-bromo)benzoyloxy-5,6-dihydro-phenanthridine (10p): $^1$H NMR (400 MHz, CDCl$_3$) δ 8.02-7.85 (m, 5H), 7.72 (s, 1H), 7.59-7.46 (m, 6H), 7.32-7.30 (m, 1H), 4.11 (s, 2H), 2.82 (d, J=7.2 Hz, 2H), 2.54 (s, 3H), 1.31 (d, J=7.3 Hz, 3H); $^{13}$C NMR (151 MHz, CDCl$_3$) δ 171.28 (C), 170.97 (C), 151.45 (C), 143.64 (C), 137.46 (2CH), 137.42 (2CH), 136.27 (C), 133.28 (2CH), 133.20 (2CH), 134.96 (C), 130.98 (CH), 130.43 (C), 129.76 (CH), 128.64 (C), 128.59 (C), 125.41 (C), 125.33 (C), 123.78 (CH), 123.30 (CH), 120.81 (C), 116.59 (C), 113.51 (CH), 58.94 (CH$_2$), 40.09 (CH$_3$), 24.92 (CH$_2$), 15.35 (CH$_3$). HREIMS m/z 619.0009 [M]$^+$ (calcd for C$_{30}$H$_{23}$Br$_2$NO$_4$, 618.9994).

4-ethenyl-5-methyl-5,6-dihydrophenanthridine-8,9-diol (11): $^1$H NMR (400 MHz, DMSO) δ 7.59-7.49 (m, 2H), 7.41 (d, J=7.6 Hz, 1H), 7.19-7.08 (m, 2H), 6.65 (s, 1H), 5.76 (d, J=17.9 Hz, 1H), 5.27 (d, J=11.4 Hz, 1H), 4.23 (s, 2H), 3.87 (s, 3H); $^{13}$C NMR (150 MHz, DMSO) δ 153.39 (C), 149.58 (C), 138.22 (CH), 133.15 (CH), 132.75 (C), 132.05 (C), 131.04 (C), 128.92 (CH), 125.57 (C), 123.98 (CH), 118.65 (C), 118.39 (CH$_2$), 113.46 (CH), 107.33 (CH), 62.34 (CH$_2$), 50.72 (CH$_3$); HREIMS m/z 253.1109 [M]$^+$ (calcd for C$_{16}$H$_{15}$NO$_2$, 253.1103).

4-ethenyl-5-methyl-8,9-diallyloxy-5,6-dihydro-phenanthridine (11a): $^1$H NMR (600 MHz, CDCl$_3$) δ 7.64 (d, J=7.6 Hz, 1H), 7.53 (d, J=6.7 Hz, 1H), 7.49 (t, J=7.8 Hz, 2H), 7.27 (s, 1H), 6.85 (s, 1H), 6.12-6.02 (m, 2H), 5.81 (d, J=16.6 Hz, 1H), 5.63 (d, J=11.9 Hz, 2H), 5.48-5.42 (m, 5H), 5.34 (s, 2H), 5.32 (s, 2H), 2.88 (s, 3H); $^{13}$C NMR (151 MHz, CDCl$_3$) δ 161.46 (C), 154.36 (C), 149.73 (C), 137.83 (CH), 136.78 (CH), 133.34 (CH), 133.29 (CH), 129.98 (C), 127.21 (C), 124.76 (CH), 123.90 (CH), 120.83 (C), 117.32 (C), 116.43 (CH$_2$), 116.40 (CH$_2$), 111.48 (CH$_2$), 110.43 (CH$_2$), 107.14 (CH), 69.24 (CH$_2$), 69.17 (CH$_2$), 61.47 (CH$_2$), 40.17 (CH$_3$); HREIMS m/z 333.1720 [M]$^+$ (calcd for C$_{22}$H$_{23}$NO$_2$, 333.1729).

4-ethenyl-5-methyl-8,9-di(prop-2-ynyloxy)-5,6-dihydro-phenanthridine (11b): $^1$H NMR (400 MHz, CDCl$_3$) δ 7.62 (s, 1H), 7.48 (d, J=12.4 Hz, 2H), 7.24-7.14 (m, 2H), 6.92 (s, 1H), 5.75 (d, J=19.0 Hz, 1H), 5.32 (d, J=10.6 Hz, 1H), 4.88-4.77 (m, 4H), 4.06 (s, 2H), 2.56 (s, 1H), 2.55 (s, 1H), 2.52 (s, 3H); $^{13}$C NMR (151 MHz, CDCl$_3$) δ 159.12 (C), 156.17 (C), 146.12 (C), 139.32 (CH), 133.72 (CH), 129.17 (C), 127.56 (C), 124.57 (CH), 123.30 (CH), 120.88 (C), 118.76 (C), 114.12 (CH$_2$), 110.63 (CH), 106.21 (CH), 80.14 (C), 80.09 (C), 76.42 (CH), 76.36 (CH), 64.78 (CH$_2$), 64.71 (CH$_2$), 58.83 (CH$_2$), 42.68 (CH$_3$); HREIMS m/z 329.1420 [M]$^+$ (calcd for C$_{22}$H$_{19}$NO$_2$, 329.1416).

4-ethenyl-5-methyl-8,9-bis-cyclobutylmethoxy-5,6-dihydro-phenanthridine (11c): $^1$H NMR (400 MHz, CDCl$_3$) δ 7.98 (d, J=7.5 Hz, 1H), 7.58-7.51 (m, 1H), 7.43 (s, 1H), 7.43-7.29 (m, 2H), 6.97 (t, J=7.5 Hz, 7.2 Hz, 1H), 5.76-5.52 (m, 2H), 4.61 (s, 2H), 3.98 (d, J=7.1 Hz, 2H), 3.96 (d, J=7.1 Hz, 2H), 3.07 (s, 3H), 2.46-2.28 (m, 2H), 2.17-1.73 (m, 12H); $^{13}$C NMR (100 MHz, CDCl$_3$) δ 159.23 (C), 152.17 (C), 150.87 (C), 136.98 (CH), 131.24 (CH), 128.12 (C), 125.74 (C), 121.54 (CH), 121.01 (CH), 120.82 (C), 119.17 (C), 116.77 (CH), 114.04 (CH$_2$), 108.68 (CH), 105.17 (CH), 63.64 (CH$_2$), 63.61 (CH$_2$), 42.18 (CH$_3$) 33.41 (CH), 33.38 (CH), 25.78 (2CH$_2$), 25.74 (2CH$_2$), 15.02 (CH$_2$), 14.99 (CH$_2$); HREIMS m/z 389.2350 [M]$^+$ (calcd for C$_{26}$H$_{31}$NO$_2$, 389.2355).

4-ethenyl-5-methyl-8,9-bis-cyclohexylmethoxy-5,6-dihydro-phenanthridine (11d): $^1$H NMR (400 MHz, CDCl$_3$) δ 8.02 (d, J=7.3 Hz, 1H), 7.47-7.41 (m, 2H), 7.39-7.31 (m, 2H), 7.02 (t, J=7.5 Hz, 7.2 Hz, 1H), 5.82-5.69 (m, 2H), 4.72 (s, 2H), 3.98-3.69 (m, 4H), 2.99 (s, 3H), 2.11-1.63 (m, 12H), 1.52-1.33 (m, 4H), 1.31-0.96 (m, 6H); $^{13}$C NMR (100 MHz, CDCl$_3$) δ 159.76 (C), 153.57 (C), 151.23 (C), 137.42 (CH), 132.62 (CH), 129.78 (C), 125.07 (C), 122.13 (CH), 121.78 (CH), 120.23 (C), 118.87 (C), 115.32 (CH), 112.76 (CH$_2$), 107.19 (CH$_2$), 105.87 (CH), 66.78 (CH$_2$), 66.73 (CH$_2$), 40.18 (CH$_3$), 31.63 (CH), 31.60 (CH), 26.35 (2CH$_2$), 26.31 (2CH$_2$), 25.97 (CH$_2$), 25.92 (CH$_2$), 24.31 (2CH$_2$), 24.28 (2CH$_2$); HREIMS m/z 445.1972 [M]$^+$ (calcd for C$_{30}$H$_{39}$NO$_2$, 445.2981).

4-ethenyl-5-methyl-8,9-dibenzyloxy-5,6-dihydro-phenanthridine (11e): $^1$H NMR (400 MHz, CDCl$_3$) δ 7.72 (d, J=7.5 Hz, 1H), 7.63-7.55 (m, 4H), 7.46-7.42 (m, 3H), 7.39-7.31 (m, 4H), 7.29 (s, 1H), 7.22-7.16 (m, 2H), 7.11 (s, 1H), 5.94 (d, J=22.8 Hz, 1H), 5.81 (d, J=22.5 Hz, 1H), 5.42 (s, 2H), 5.40 (s, 2H), 4.92 (s, 2H), 2.92 (s, 3H); $^{13}$C NMR (100 MHz, CDCl$_3$) δ 153.23 (C), 149.13 (C), 148.97 (C), 141.88 (C), 141.67 (C), 135.67 (CH), 132.01 (CH), 131.96 (CH), 129.96 (2CH), 129.79 (2CH), 129.42 (2CH), 129.24 (2CH), 127.93 (CH), 126.24 (C), 125.14 (CH), 123.78 (CH), 122.66 (C), 117.27 (C), 116.05 (C), 113.58 (CH$_2$), 112.89 (CH), 111.15 (CH), 72.56 (CH$_2$), 72.47 (CH$_2$), 54.52 (CH$_2$), 40.18 (CH$_3$); HREIMS m/z 433.2037 [M]$^+$ (calcd for C$_{30}$H$_{27}$NO$_2$, 433.2042).

4-ethenyl-5-methyl-8,9-di(2,3-dimethoxy)benzyloxy-5,6-dihydro-phenanthridine (11 f): $^1$H NMR (400 MHz, CDCl$_3$) δ 7.68-7.61 (m, 2H), 7.41-7.32 (m, 4H), 7.29-7.24 (m, 2H), 7.15-7.18 (m, 2H), 7.09-7.00 (m, 2H), 5.81 (d, J=16.9 Hz, 1H), 5.52 (d, J=16.8 Hz, 1H), 5.38 (s, 2H), 5.36 (s, 2H), 4.78 (s, 2H), 3.90 (s, 3H), 3.91 (s, 3H), 3.89 (s, 3H), 3.88 (s, 3H), 3.85 (s, 3H); $^{13}$C NMR (101 MHz, CDCl$_3$) δ 155.41 (C), 152.18 (C), 143.38 (C), 143.26 (C), 141.82 (C), 141.51 (C), 139.75 (CH), 136.23 (CH), 134.76 (C), 134.65 (C), 133.18 (C), 132.96 (CH), 132.41 (CH), 131.94 (C), 131.92 (CH), 131.67 (CH), 128.53 (C), 125.16 (CH), 123.17 (CH), 123.06 (CH), 122.32 (CH), 122.18 (CH), 119.67 (C), 118.88 (CH$_2$), 116.42 (C), 109.83 (CH), 67.76 (CH$_2$), 65.92 (CH$_2$), 65.60 (CH$_2$), 62.10 (CH$_3$), 62.04 (CH$_3$), 60.87 (CH$_3$), 60.34 (CH$_3$), 52.36 (CH$_3$); HREIMS m/z 553.2452 [M]$^+$ (calcd for C$_{34}$H$_{35}$NO$_6$, 553.2464).

4-ethenyl-5-methyl-8,9-di(4-cyano)benzyloxy-5,6-dihydro-phenanthridine (11 g): $^1$H NMR (400 MHz, CDCl$_3$) δ 7.68 (m, 1H), 7.57 (d, J=8.2 Hz, 4H), 7.50 (d, J=8.3 Hz, 4H), 7.23-7.19 (m, 5H), 5.58 (d, J=13.9 Hz, 1H), 5.41 (d, J=13.9 Hz, 1H), 4.51-4.46 (m, 4H), 4.46 (s, 2H), 3.01 (s, 3H); $^{13}$C NMR (100 MHz, CDCl$_3$) δ 155.17 (C), 149.68 (C), 148.07 (C), 142.23 (C), 142.29 (C), 136.77 (CH), 131.76 (2CH), 131.73 (2CH), 129.57 (2CH), 129.53 (2CH), 128.61 (CH), 125.92 (C), 124.64 (CH), 123.56 (CH), 121.98 (C), 119.28 (C), 119.22 (C), 116.53 (C), 116.58 (C), 115.85 (C), 116.55 (C), 114.42 (CH$_2$), 112.34 (CH), 111.25 (CH), 70.36 (CH$_2$), 70.31 (CH$_2$), 58.97 (CH$_2$), 40.18 (CH$_3$); HREIMS m/z 483.1940 [M]$^+$ (calcd for C$_{32}$H$_{25}$N$_3$O$_2$, 483.1947).

4-ethenyl-5-methyl-8,9-diacetoxy-5,6-dihydro-phenanthridine (11h): $^1$H NMR (400 MHz, CDCl$_3$) δ 7.92 (d, J=7.4 Hz, 1H), 7.69 (s, 1H), 7.57 (d, J=7.5 Hz, 1H), 7.38-7.26 (m, 2H), 7.21 (s, 1H), 5.82-5.73 (m, 2H), 4.07 (s, 2H), 3.13 (s, 3H), 2.71-2.62 (m, 6H); $^{13}$C NMR (100 MHz, CDCl$_3$) δ 171.89 (C), 171.84 (C), 149.76 (C), 147.23 (C), 139.79 (C), 139.43 (C), 136.82 (C), 132.61 (CH), 127.83 (CH), 127.148

(CH), 126.56 (CH), 125.21 (C), 123.97 (C), 122.96 (CH), 121.32 (CH), 113.17 (CH$_2$), 59.72 (CH$_2$), 40.17 (CH$_3$), 24.13 (CH$_3$), 24.10 (CH$_3$); HREIMS m/z 337.1308 [M]$^+$ (calcd for C$_{20}$H$_{19}$NO$_4$, 337.1314).

4-ethenyl-5-methyl-8,9-dipropionyloxy-5,6-dihydro-phenanthridine (11i): $^1$H NMR (600 MHz, CDCl$_3$) δ 7.60 (d, J=6.9 Hz, 1H), 7.52 (s, 1H), 7.49 (d, J=7.5 Hz, 1H), 7.28 (m, 1H), 7.19-7.13 (m, 1H), 7.08 (s, 1H), 5.73 (d, J=17.3 Hz, 1H), 5.33 (d, J=17.3 Hz, 1H), 4.10 (s, 2H), 3.06 (s, 3H), 2.61-2.56 (m, 4H), 2.53 (s, 3H), 1.29-1.22 (m, 6H). $^{13}$C NMR (151 MHz, CDCl$_3$) δ 172.34 (C), 172.17 (C), 145.72 (C), 144.32 (C), 140.53 (C), 139.92 (C), 135.75 (C), 131.34 (CH), 128.78 (CH), 127.58 (CH), 127.49 (CH), 125.84 (C), 124.11 (C), 123.21 (CH), 121.73 (CH), 116.88 (CH$_2$), 60.57 (CH$_2$), 43.23 (CH$_3$), 25.23 (CH$_2$), 25.20 (CH$_2$), 18.78 (CH$_3$), 18.74 (CH$_3$); HREIMS m/z 365.1635 [M]$^+$ (calcd for C$_{22}$H$_{23}$NO$_4$, 365.1627).

4-ethenyl-5-methyl-8,9-diisobutyryloxy-5,6-dihydro-phenanthridine (11j): $^1$H NMR (600 MHz, CDCl$_3$) δ 7.91 (d, J=7.3 Hz, 1H), 7.64 (s, 1H), 7.56 (d, J=7.3 Hz, 1H), 7.42-7.39 (m, 1H), 7.33-7.27 (m, 1H), 7.17 (s, 1H), 5.85-5.72 (m, 2H), 4.02 (s, 2H), 3.06 (s, 3H), 2.58-2.47 (d, J=49.9 Hz, 2H), 1.41-1.04 (m, 12H); $^{13}$C NMR (151 MHz, CDCl$_3$) δ 173.03 (C), 173.00 (C), 149.65 (C), 145.37 (C), 141.68 (C), 140.12 (C), 136.33 (C), 132.14 (CH), 129.82 (CH), 128.31 (CH), 127.17 (CH), 125.01 (CH), 124.57 (C), 121.76 (CH), 120.89 (CH), 113.12 (CH$_2$), 58.67 (CH$_2$), 41.31 (CH$_3$), 31.67 (CH), 31.64 (CH), 16.48 (2CH$_3$), 16.42 (2CH$_3$); HREIMS m/z 393.1944 [M]$^+$ (calcd for C$_{24}$H$_{27}$NO$_4$, 393.1940).

4-ethenyl-5-methyl-8,9-divaleryoxy-5,6-dihydro-phenanthridine (11k): $^1$H NMR (600 MHz, CDCl$_3$) δ 7.95 (d, J=7.6 Hz, 1H), 7.63 (s, 1H), 7.59 (d, J=7.8 Hz, 1H), 7.47 (t, J=7.7 Hz, 1H), 7.28 (t, J=11.6 Hz, 1H), 7.17 (s, 1H), 5.03 (dd, J=10.5, 2.7 Hz, 1H), 4.82 (t, J=10.3 Hz, 1H), 4.73 (s, 2H), 2.99 (s, 3H), 2.57 (overlap, 4H), 1.79-1.68 (m, 4H), 1.50-1.38 (m, 4H), 1.00-0.93 (m, 6H); $^{13}$C NMR (151 MHz, CDCl$_3$) δ 171.21 (C), 171.10 (C), 143.26 (C), 143.08 (C), 141.03 (C), 139.62 (C), 136.28 (C), 130.73 (CH), 129.12 (CH), 127.27 (CH), 127.22 (CH), 126.35 (C), 124.94 (C), 123.60 (CH), 122.23 (CH), 119.27 (CH$_2$), 58.05 (CH$_2$), 46.56 (CH$_3$), 35.63 (CH$_2$), 33.97 (CH$_2$), 27.11 (2CH$_2$), 22.48 (CH$_2$), 22.45 (CH$_2$), 13.96 (2CH$_3$). HREIMS m/z 421.2242 [M]$^+$ (calcd for C$_{26}$H$_{31}$NO$_4$, 421.2253).

4-ethenyl-5-methyl-8,9-diisovaleroxy-5,6-dihydro-phenanthridine (11l): $^1$H NMR (600 MHz, CDCl$_3$) δ 7.85 (d, J=7.0 Hz, 1H), 7.72 (d, J=5.3 Hz, 1H), 7.64 (s, 1H), 7.62 (dd, J=7.9, 1.0 Hz, 1H), 7.52 (dd, J=9.8, 5.7 Hz, 1H), 7.22 (s, 1H), 5.83 (d, J=16.4 Hz, 1H), 5.71 (d, J=11.3 Hz, 1H), 5.04 (s, 2H), 2.92 (s, 3H), 2.53 (d, J=2.4 Hz, 2H), 2.52 (d, J=2.4 Hz, 2H), 2.26-2.18 (m, 2H), 1.09 (d, J=3.4 Hz, 6H), 1.07 (d, J=3.4 Hz, 6H); $^{13}$C NMR (151 MHz, CDCl$_3$) δ 170.45 (C), 170.38 (C), 139.97 (C), 139.53 (C), 138.07 (CH), 137.03 (CH), 135.53 (C), 130.92 (CH), 130.16 (CH), 126.73 (C), 125.41 (C), 124.22 (CH), 120.84 (CH), 116.99 (CH), 111.32 (CH$_2$), 106.81 (CH), 55.95 (CH$_2$), 43.18 (CH$_3$), 42.73 (CH$_2$), 42.70 (CH$_2$), 29.98 (CH), 29.92 (CH), 25.52 (4CH$_3$). HREIMS m/z 421.2251 [M]$^+$ (calcd for C$_{26}$H$_{31}$NO$_4$, 421.2253).

4-ethenyl-5-methyl-8,9-dibenzoyloxy-5,6-dihydro-phenanthridine (11m): $^1$H NMR (400 MHz, CDCl$_3$) δ 8.07 (d, J=8.2 Hz, 5H), 7.91 (d, J=7.4 Hz, 1H), 7.73 (d, J=7.4 Hz, 1H), 7.62-7.50 (m, 4H), 7.42 (dd, J=17.2, 9.2 Hz, 5H), 5.34 (d, J=17.8 Hz, 1H), 5.13 (d, J=17.8 Hz, 1H), 4.72 (d, 2H), 3.03 (s, 3H). $^{13}$C NMR (151 MHz, CDCl$_3$) δ 172.56 (C), 172.41 (C), 145.73 (C), 143.28 (C), 142.87 (C), 139.76 (C), 137.53 (C), 132.94 (C), 132.88 (C), 132.62 (C), 131.78 (CH), 131.71 (CH), 130.46 (2CH), 130.42 (2CH), 129.78 (CH), 128.32 (CH), 127.68 (2CH), 127.54 (2CH), 127.24 (CH), 125.73 (C), 124.13 (C), 123.87 (CH), 122.09 (CH), 120.32 (CH$_2$), 58.94 (CH$_2$), 41.23 (CH$_3$). HREIMS m/z 461.1637 [M]$^+$ (calcd for C$_{30}$H$_{23}$NO$_4$, 461.1627).

4-ethenyl-5-methyl-8,9-di(4-bromo)benzoyloxy-5,6-di-hydro-phenanthridine (11n): $^1$H NMR (400 MHz, CDCl$_3$) δ 8.02-7.93 (m, 5H), 7.88-7.82 (m, 4H), 7.72 (s, 1H), 7.68 (s, 1H), 7.43-7.36 (m, 1H), 7.25-7.21 (m, 1H), 6.98 (s, 1H), 5.99-5.71 (m, 2H), 4.68 (s, 2H), 3.11 (s, 3H); $^{13}$C NMR (100 MHz, CDCl$_3$) δ 171.88 (C), 171.76 (C), 145.17 (C), 142.97 (C), 142.12 (C), 140.23 (C), 136.97 (C), 133.86 (2CH), 133.83 (2CH), 131.37 (2CH), 131.33 (2CH), 132.88 (CH), 129.78 (C), 128.87 (C), 128.81 (C), 127.97 (CH), 127.68 (CH), 126.37 (C), 126.35 (C), 125.14 (C), 123.78 (C), 123.21 (CH), 122.76 (CH), 119.83 (CH$_2$), 59.16 (CH$_2$), 40.87 (CH$_3$). HREIMS m/z 616.9849 [M]$^+$ (calcd for C$_{30}$H$_{21}$BrNO$_4$, 616.9837).

4-ethyl-5-methyl-8,9-bis[1-(2-amino-ethyl)-1H-[1,2,3] triazol-4-ylmethoxy]-5,6-dihydro-phenanthridine (10q): $^1$H NMR (400 MHz, CDCl$_3$) δ: 7.78 (m, 1H), 7.51-7.41 (m, 3H), 7.15-7.08 (m, 3H), 5.23-5.16 (m, 8H), 4.52-4.43 (m, 2H), 4.42 (s, 1H), 3.50 (s, 2H), 3.45 (s, 2H), 2.78 (d, J=8 Hz, 2H), 2.44 (s, 3H), 1.27 (t, J=8.0 Hz, 3H); $^{13}$C NMR (100 MHz, CDCl$_3$) δ: 147.17 (C), 144.05 (C), 139.44 (C), 135.99 (C), 134.83 (C), 134.03 (C), 128.80 (C), 128.44 (C), 124.75 (CH), 124.51 (CH), 121.62 (CH), 121.55 (CH), 115.64 (C), 115.55 (C), 110.23 (CH), 109.84 (CH), 64.27 (CH$_2$), 63.26 (CH$_2$), 54.96 (CH$_2$), 50.78 (CH$_2$), 50.61 (CH$_2$), 41.65 (CH$_3$), 40.29 (CH$_2$), 39.41 (CH$_2$), 29.91 (CH$_2$), 15.27 (CH$_3$); HREIMS m/z 503.2741 [M]+(calcd for C$_{26}$H$_{33}$N$_9$O$_2$, 503.2757).

4-ethyl-5-methyl-8,9-bis[1-(2-acetylamino-ethyl)-1H-[1, 2,3]triazol-4-ylmethoxy]-5,6-dihydro-phenanthridine (10r): $^1$H NMR (500 MHz, CDCl$_3$) δ 7.99 (s, 1H), 7.89-7.81 (m, 2H), 7.47 (s, 1H), 7.32-7.29 (m, 2H), 7.13 (dd, J=16.0, 3.7 Hz, 1H), 5.56-5.42 (m, 3H), 5.41-5.12 (m, 5H), 4.58-4.43 (m, 2H), 3.80-3.64 (m, 4H), 2.79 (m, 2H), 2.68 (s, 3H), 1.92 (s, 3H), 1.90 (s, 3H), 1.25 (m, 3H); $^{13}$C NMR (125 MHz, CDCl$_3$) δ 172.2, 171.9, 149.7, 149.4, 146.1, 142.9, 142.6, 130.7, 129.3, 126.1, 125.1, 124.8, 124.4, 122.7, 122.0, 121.9, 112.6, 110.9, 56.2, 56.0, 51.4, 50.4, 50.3, 39.8, 36.8, 36.3, 28.6, 27.1, 26.9, 14.1.HREIMS m/z 587.2960 [M]+ (calcd for C$_{30}$H$_{37}$N$_9$O$_4$, 587.2969).

4-ethenyl-5-methyl-8,9-bis[1-(2-amino-ethyl)-1H-[1,2,3] triazol-4-ylmethoxy]-5,6-dihydrophenanthridine (11q): $^1$H NMR (500 MHz, CDCl$_3$) δ 7.92 (s, 1H), 7.88-7.84 (m, 1H), 7.61 (s, 1H), 7.44-7.27 (m, 2H), 7.19-7.12 (m, 2H), 6.97-6.88 (m, 1H), 5.81-5.73 (m, 2H), 5.68-5.51 (m, 5H), 5.19 (s, 2H), 5.11 (s, 2H), 4.94 (s, 1H), 4.67 (s, 1H), 3.33-3.21 (m, 4H), 2.77 (s, 3H); $^{13}$C NMR (125 MHz, CDCl$_3$) δ 150.4, 148.1, 146.6, 144.1, 143.9, 137.7, 128.2, 126.1, 125.9, 125.3, 125.1, 124.1, 123.3, 123.0, 115.3, 115.1, 113.8, 111.1, 59.1, 58.8, 52.4, 52.2, 49.1, 40.3, 40.2, 39.9; HREIMS m/z 501.2613 [M]$^+$ (calcd for C$_{26}$H$_{31}$N$_9$O$_2$, 501.2601).

4-ethenyl-5-methyl-8,9-bis[1-(2-acetylamino-ethyl)-1H-[1,2,3]triazol-4-ylmethoxy]-5,6-dihydro-phenanthridine (11r): $^1$H NMR (500 MHz, CDCl$_3$) δ 7.93-7.91 (m, 1H), 7.86 (s, 1H), 7.69 (s, 1H), 7.51-7.37 (m, 2H), 7.28-7.15 (m, 2H), 6.91-6.84 (m, 1H), 5.88-5.79 (m, 1H), 5.62-5.50 (m, 5H), 5.14 (s, 2H), 5.10 (s, 2H), 4.76 (s, 1H), 4.62 (s, 1H), 3.67-3.54 (m, 4H), 2.98 (s, 3H), 1.94 (s, 3H), 1.91 (s, 3H); $^{13}$C NMR (125 MHz, CDCl$_3$) δ 174.3, 174.2, 150.1, 148.9, 146.4, 143.8, 143.6, 138.7, 128.6, 126.8, 125.8, 125.2, 125.0, 122.8, 121.3, 121.1, 116.4, 115.1, 112.6, 111.0, 55.70, 55.6, 50.7, 51.4, 51.3, 39.8, 36.8, 36.6, 22.4, 22.1; HREIMS m/z 585.2821 [M]$^+$ (calcd for C$_{30}$H$_{35}$N$_9$O$_4$, 585.2812).

Example 3: Anti-Hepatitis C Virus (HCV) Activity of the Compound of the Present Invention (A) Experimental Methods (1) Toxicity Experiment of the Compound on Huh7.5:

100 μL of Huh7.5 cells (1×10$^5$/ml) was inoculated in 96-wells plates and incubated in an incubator at 37° C. under 5% of $CO_2$ and saturated humidity for 24 hrs. Then different concentration of the compound of the present invention and positive control (VX-950, telaprevir) were added respectively and incubated for a further 72 hrs. 10 μL of MTT (5 mg/mL) was added per well and incubated for another 4 hrs. After the cells were lysed with DMSO, $OD_{570\text{-}630\ mm}$ was determined on ELIASA. In comparison with OD of the control group, inhibitory rate of each concentration on cell toxicity was calculated, and half toxic concentration of the compound was calculated with Reed-Muench method.

(2) Anti-HCV Activity of the Compound in Cells:

100 μL of Huh7.5 cells (1×10$^5$/ml) was inoculated in 96-well plates and incubated in a incubator at 37° C. under 5% of $CO_2$ and saturated humidity for 24 hrs. Then Huh7.5 cells were infected with virus containing recombinant whole-genome HCV virus particles (Zong-Gen Peng, Bo Fan, Na-Na Du, et al. Small Molecular Compounds that Inhibit Hepatitis C Virus Replication Through Destabilizing Heat Shock Cognate 70 Messenger RNA. HEPATOLOGY, Vol. 52, No. 3, 2010, 845-853.), meanwhile, the compound of the present invention with different concentration and positive control (VX-950, telaprevir) were added respectively and incubated for a further 72 hrs. The total RNA was extracted from the cells. The intracellular content of HCV and RNA of internal control gene GAPDH were determined by real-time fluorescence qRT-PCR. In comparison with the viral RNA levels of the control group, the inhibition rate on HCV of each concentration was calculated with relative quantification method ($1\text{-}2^{\Delta\Delta CT}$), and half effective concentration of the compound on HCV inhibition was calculated by Reed-Muench method.

(3) Test Results of Anti-HCV Activity:

TABLE 3-3a

Screening results of anti-HCV activity of the compound of the present invention

| Comp. | Max Tested Concentration | $CC_{50}$ (μM) | $EC_{50}$ (μM) | SD |
|---|---|---|---|---|
| 10 | 100 μM | 61.3 ± 8.4 | >11.11 ± 0.00 | — |
| 11 | 100 μM | >100 ± 0 | 8.37 ± 2.39 | 12 |
| 10a | 100 μM | >100 ± 0 | <0.41 ± 0.00 | >244 |
| 10b | 100 μM | >100 ± 0 | 1.63 ± 1.22 | >61 |
| 10c | 100 μM | >100 ± 0 | 16.30 ± 10.07 | >6 |
| 10d | 100 μM | 58.3 ± 2.1 | 0.83 ± 0.35 | 70 |
| 10e | 100 μM | >100 ± 0.00 | 9.50 ± 2.71 | >10.5 |
| 10f | 100 μM | >100 ± 0.00 | 10.84 ± 2.86 | >9.2 |
| 10g | 100 μM | 30.2 ± 0.6 | 1.25 ± 0.56 | 24 |
| 10h | 100 μM | >100 ± 0 | 4.32 ± 0.10 | >23 |
| 10j | 100 μM | 90.1 ± 7.4 | 0.23 ± 0.08 | 388 |
| 11a | 100 μM | >100 ± 0 | 28.75 ± 5.38 | >3 |
| 11b | 100 μM | >100 ± 0 | 4.20 ± 1.72 | >24 |
| 11c | 100 μM | >100 ± 0.00 | 11.29 ± 1.66 | >8.8 |
| 11d | 100 μM | >100 ± 0.00 | >33.33 ± 0.00 | 3 |
| 11e | 100 μM | >100 ± 0.00 | 13.42 ± 0.98 | >7.5 |
| 11f | 100 μM | 32.87 ± 1.28 | 0.30 ± 0.01 | 109.3 |
| 11g | 100 μM | 25.88 ± 0.82 | >0.37 ± 0.00 | <69.9 |
| VX-950 | 100 μg/mL | 39.5 ± 4.9 | 0.20 ± 0.04 | 193 |

TABLE 3-3b

Screening results of anti-HCV activity of the compound of the present invention

| Comp. | Max Tested Concentration | $CC_{50}$ (μM) | $EC_{50}$ (μM) | SD |
|---|---|---|---|---|
| 10l | 100 μM | >100 ± 0 | 13.91 ± 11.39 | >7 |
| 10m | 100 μM | >100 ± 0.00 | 9.39 ± 0.46 | >10.6 |
| 10n | 100 μM | 50.3 ± 1.0 | 1.43 ± 0.45 | 35 |
| 10o | 100 μM | 91.49 ± 4.19 | 11.03 ± 2.23 | 8.2 |
| 10p | 100 μM | >100 ± 0 | 1.19 ± 0.02 | >84 |
| 11h | 100 μM | >100 ± 0 | 1.63 ± 0.91 | >61 |
| 11i | 100 μM | >100 ± 0.00 | 1.02 ± 0.16 | >97.8 |
| 11j | 100 μM | >100 ± 0.00 | 1.83 ± 0.17 | >54.6 |
| 11k | 100 μM | >100 ± 0.00 | 0.94 ± 0.02 | 106.8 |
| 11l | 100 μM | >100 ± 0 | 3.27 ± 1.26 | >31 |
| 11m | 100 μM | >100 ± 0.00 | 1.03 ± 0.07 | >96.8 |
| 11n | 100 μM | 82.60 ± 3.28 | 4.58 ± 0.55 | 18.1 |
| VX-950 | 100 μg/mL | 32.53 ± 0.58 | 0.088 ± 0.005 | 370.8 |

Example 4

The activity of compounds 10q, 10r, 11q, and 11r of the present invention on Wnt signaling pathway activation:

Activity Assay of the Reporter Gene

HEK293T, HCT116, SW480 or NIH3T3 cells used for activity assay of the reporter gene were inoculated into 24-wells plates respectively 24 hours before transfection then transfected following the above mentioned reference method. The amount of the plasmids used for Transfection was: 20 ng of TOPFlash, NFAT-Luc, or SRF-Luc, and 25 ng of EGFP-C1 (HEK293T); 25 ng of LEF-Luc, 75 ng of LEF1, and 25 ng of EGFP-C1 (NIH3T3); 100 ng of TOPFlash or Fopfllash and 100 ng of EGFP-C1 (HCT116 and SW480). The cells were transfected with other plasmids following experimental requirements, LacZs were added to meet a total content of 250 ng (in RNAi and plasmid co-transfection experiments, 1 μl of siRNA was added when every 100 ng/well of the plasmid was transfected). Wnt3a conditioned medium was added 18 hours after transfection to stimulate the cells for 6-8 hours, the cells were lysed using Boehringer Mannheim Luci-ferase Assay Kit (200 μl/well). Intensity of GFP proteins in cell lysates were determined as internal standards of expression quantity of the cells using fluorescence meter FL600 (BIO-TEK Inc. Winooski, Vt.), and then 20 μl of luciferase substrates were added. Luciferase activity was determined with Micro Lumate Plus (Perkin Elmer Inc. Wellesley, Mass.) luminometer. Finally, the luciferase activity was homogenized using activity of GFP.

Determination of Intracellular Free β-Catenin

HEK293T cells (in 6-wells plate) were stimulated with Wnt3a conditioned medium for 4 hours and collected into EP tubes using pre-cooled PBS, the tubes were centrifuged at 4° C. 3000 rpm for 5 min to remove PBS. The cells were suspended using hypotonic buffer (10 mM HEPES-KOH, pH 7.9, 1.5 mM $MgCl_2$, 1 mM EDTA, 10 mM KCl, supplemented with protease inhibitors, NaF and $Na_3VO_4$ before use) and placed on ice for 10 minutes and aspirated 6-8 times using insulin needles. The suspensions were centrifuged at 3000 rpm for 5 minutes, the obtained supernatants were ultracentrifuged at 100000 g, 4° C. for 1 hour, and the resultant supernatants were used for preparing cytoplasm samples. The precipitate obtained from centrifugation under 3000 rpm for 5 minutes were rinsed 3 times using hypotonic buffer and centrifuged at 4° C., 3000 rpm for 5 min to remove the hypotonic buffer, then suspended by hypertonic buffer (20 mM HEPES, pH7.9, 1.5 mMMgCl$_2$, 420 mM NaCl, 0.2 mMEDTA, 10 mMNaF, 2 mMNa$_3$VO$_4$, 1 mM pyrophosphoric acid, supplemented with protease inhibitors, NaF, and Na$_3$VO$_4$ before use) and ultracentrifugated at 100000 g, 4° C. for 1 hour after placed on ice for 30 min, and the resultant supernatants were used for preparing nucleus samples. After SDS-PAGE gel electrophoresis, a Western blot was performed by using specific antibodies aganist β-catenin, and free β-catenins in the cytoplasm samples and the nucleus samples were determined. Specific experimental method may refer to Sheng Wang, Junlin Yin, Duozhi Chen, et al. Small-molecule modulation of Wnt signaling via modulating the Axin-LRP5/6 interaction. Nature CHEMICAL BIOLOGY, vol 9, SEPTEMBER 2013, 579-585, published online: 28 Jul. 2013, doi: 10.1038/nchembio.1309.

TABLE 4

The activity of the compound on Wnt signaling pathway activation

| Sample name | Concentration of compounds for doubly synergetic activating Wnt reporter gene |
|---|---|
| Compound 9 | 3.75 μM |
| Compound 10q | 1.25 μM |
| Compound 11q | 2.5 μM |
| Compound 10r | 1.25 μM |
| Compound 11r | 5 μM |

The Experiment Results

Compounds 9, 10q, 10r, 11q, and 11r may activate the reporter gene systems of classical Wnt signaling pathway in the way of depending on Wnt3a receptors.

Example 5: Tablets of Pharmaceutical Composition Comprising the Compound of Example 2

Preparation of tablets of pharmaceutical composition comprising the compound of Example 2 of the present invention as active agent: the compound of Example 2 was used as pharmaceutical active agent, and the excipient in Table 4 was used as auxiliary material. Tablets samples were prepared according to proportion, wherein each of the tablets samples contained 5~60 mg of the compound of Example 2. Table 4 showed the formulation of conventional tablets:

TABLE 4 drug and excipient Formulas of tablets of the pharmaceutical composition of the compound of Example 2:

| materials (mg) | Dosage | | | | | | |
|---|---|---|---|---|---|---|---|
| | Formula 1 | Formula 2 | Formula 3 | Formula 4 | Formula 5 | Formula 6 | Formula 7 |
| compounds of Example 1 and 2 | 5.0 | 10.0 | 20.0 | 30.0 | 40.0 | 50.0 | 60.0 |
| lactose | 100.0 | 100.0 | 100.0 | 100.0 | 100.0 | 100.0 | 100.0 |
| starch | 35 | 30 | 25 | 20 | 15 | 10 | 5 |
| low-substituted hydroxypropyl cellulose | 3.0 | 3.0 | 3.0 | 3.0 | 3.0 | 3.0 | 3.0 |
| micro-crystalline cellulose | 1.0 | 1.0 | 1.0 | 3.0 | 3.0 | 3.0 | 3.0 |
| talcum powder | 6.0 | 6.0 | 6.0 | 6.0 | 6.0 | 6.0 | 6.0 |
| magnesium stearate | 1.0 | 1.0 | 1.0 | 1.0 | 1.0 | 1.0 | 1.0 |
| 1% sodium hydroxy methyl cellulose | appropriate amount | appropriate amount | appropriate amount | appropriate amount | appropriate amount | appropriate amount | appropriate amount |

A preparation method of tablets with different dosages from the compound of example 2 and excipient was as follows: the excipients were uniformly mixed with the drug, then suitable amount of 1% sodium hydroxymethyl cellulose solution was added to give soft material, sieved and granulated, dried and screened the whole granulator, magnesium stearate and talcum powder were added and uniformly mixed, squashed to give the tablets.

Example 6: Capsules of Pharmaceutical Composition of the Compound of Example 2

Preparation of the capsules of the pharmaceutical composition comprising the compound of Example 2 of the present invention as active agent: the compound of Example 2 was used as pharmaceutical active agent, and the excipient in Table 5 was used as auxiliary material. The capsules samples were prepared according to proporation, wherein each of capsules samples contained 5~50 mg of the compounds of Example 2. Table 5 showed the formulas of conventional capsules:

TABLE 5

Formulas of drug and excipient of the capsules of the pharmaceutical composition of the compound of Example 2:

| materials (mg) | Dosage | | | | | |
|---|---|---|---|---|---|---|
| | Formula 1 | Formula 2 | Formula 3 | Formula 4 | Formula 5 | Formula 6 |
| compounds of Example 1 and 2 | 5.0 | 10.0 | 20.0 | 30.0 | 40.0 | 50.0 |
| lactose | — | — | — | — | — | — |
| starch | 100.0 | 90.0 | 30.0 | — | — | — |
| micro-crystalline cellulose | — | — | 50.0 | 70 | 60.0 | 50.0 |
| magnesium stearate | 1.0 | 1.0 | 1.0 | 1.0 | 1.0 | 1.0 |

TABLE 5-continued

Formulas of drug and excipient of the capsules of the pharmaceutical composition of the compound of Example 2:

| materials (mg) | Dosage | | | | | |
|---|---|---|---|---|---|---|
| | Formula 1 | Formula 2 | Formula 3 | Formula 4 | Formula 5 | Formula 6 |
| 1% sodium hydroxymethyl cellulose | appropriate amount | appropriate amount | appropriate amount | appropriate amount | appropriate amount | appropriate amount |

A method for preparing capsules comprising a certain amount of the compound of Example 2 and excipients was as follows: uniformly mixing the compound of Example 2 and the excipient, adding suitable amount of sodium hydroxymethyl cellulose solution (1%), granulating drying and screening the whole granulator, adding magnesium stearate and uniformly mixing, and filling to obtain the capsules. Alternatively, the compound of Example 2 and the excipient was mixed directly, screened and filled to prepare the capsules without granulating.

The pharmaceutical composition comprising the compound of Example 2 and various prepared and developed pharmaceutical composition comprising the compounds of Example 2 as active agents were used.

The dosage range of the compound of Example of 2: when using the compound of Example 2 as active agent, the daily dose was in the range of 5~200 mg.

Although specific embodiments of the present invention has been described in detail, those skilled in the art would understand that according to all the disclosed teaching, modification and replacement for those may be performed, and these modification and replacement are within the scope of the invention; and the full scope of the invention is delineated by the appended claims and any equivalent.

What is claimed is:

1. A compound of general formula (1),

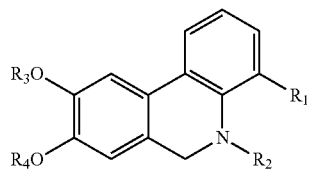

1 or a stereo isomer, a solvate, a pharmaceutically acceptable salt thereof,
wherein, $R_1$ is selected from $C_1$-$C_6$alkyl or $C_1$-$C_6$alkenyl; $R_2$ is selected from H, $C_1$-$C_6$alkyl;
$R_3$ or $R_4$ is selected from $C_1$-$C_6$alkenyl, benzyl, silyl, benzoyl, 1-(amino-$C_{1-6}$alkyl)-1H-[1,2,3]triazol-4-methyl, which is unsubstituted or substituted by a substituent, wherein the substituent is selected from $C_1$-$C_6$alkyl, $C_1$-$C_6$alkoxy, halo, $C_1$-$C_6$alkanoyl, and the number of the substituent is one, two or three.

2. The compound of general formula (1) according to claim 1, wherein $R_1$ is selected from methyl, ethyl, vinyl; $R_2$ is selected from H, methyl, ethyl; $R_3$ or $R_4$ is selected from propenyl, cyclopropylmethyl, cyclobutylmethyl, cyclohexylmethyl, benzyl, 2,3-dimethoxy-benzyl; 3,5-dimethoxybenzyl, tert-butyl-dimethylsilyl, trimethylsilyl; benzoyl, p-methoxybenzoyl, 3-methoxybenzoyl, bromobenzoyl, chlorobenzoyl, 3,5-dimethoxybenzoyl, 2,3-dimethoxybenzoyl, 3,4,5-trimethoxybenzoyl, 1-(2-amino-ethyl)-1H-[1,2,3]triazol-4-methyl, 1-(2-acetylamino-ethyl)-1H-[1,2,3]triazol-4-methyl.

3. The compound of general formula (1) according to claim 1, which has a structure of general formula (2),

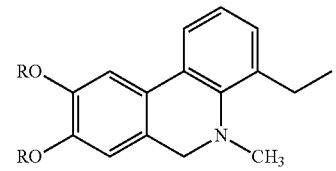

2 or a stereo isomer, a solvate, a pharmaceutically acceptable salt thereof,
Wherein, R is selected from propenyl, cyclopropylmethyl, cyclobutylmethyl, cyclohexylmethyl, benzyl, 2,3-dimethoxy-benzyl; 3,5-dimethoxybenzyl, tert-butyl-dimethylsilyl, trimethylsilyl; benzoyl, p-methoxybenzoyl, 3-methoxybenzoyl, bromobenzoyl, chlorobenzoyl, 3,5-dimethoxybenzoyl, 2,3-dimethoxybenzoyl, 3,4,5-trimethoxybenzoyl, 1-(2-amino-ethyl)-1H-[1,2,3]triazol-4-methyl, 1-(2-acetylamino-ethyl)-1H-[1,2,3]triazol-4-methyl.

4. The compound of general formula (1) according to claim 1, which has a structure of formula (3),

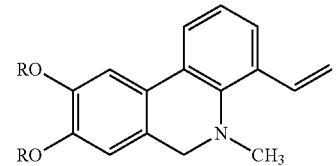

3 or a stereo isomer, a solvate, a pharmaceutically acceptable salt thereof,
Wherein, R is selected from propenyl, cyclopropylmethyl, cyclobutylmethyl, cyclohexylmethyl, benzyl, 2,3-dimethoxy-benzyl; 3,5-dimethoxybenzyl, tert-butyl-dimethylsilyl, trimethyl silyl; benzoyl, p-methoxybenzoyl, 3-methoxybenzoyl, bromobenzoyl, chlorobenzoyl, 3,5-dimethoxybenzoyl, 2,3-dimethoxybenzoyl, 3,4,5-trimethoxybenzoyl, 1-(2-amino-ethyl)-1H-[1,2,3]triazol-4-methyl, and 1-(2-acetylamino-ethyl)-1H-[1,2,3]triazol-4-methyl.

5. A compound or a stereo isomer, a solvate, a pharmaceutically acceptable salt thereof, wherein the compound is selected from
4-ethyl-5-methyl-8,9-diallyloxy-5,6-dihydro-phenanthridine (10c);
4-ethyl-5-methyl-8,9-diprop-2-ynyloxy-5,6-dihydro-phenanthridine (10d);
4-ethyl-5-methyl-8,9-bis-cyclobutylmethoxy-5,6-dihydro-phenanthridine (10e);
4-ethyl-5-methyl-8,9-bis-cyclohexylmethoxy-5,6-dihydro-phenanthridine (10f);
4-ethyl-5-methyl-8,9-dibenzyloxy-5,6-dihydro-phenanthridine (10g);
4-ethyl-5-methyl-8,9-di(2,3-dimethoxy)benzyloxy-5,6-dihydro-phenanthridine (10h);

4-ethyl-5-methyl-8,9-dibenzoyloxy-5,6-dihydro-phenan-thridine (10o);
4-ethyl-5-methyl-8,9-di(4-bromo)benzoyloxy-5,6-di-hydro-phenanthridine (10p);
4-ethenyl-5-methyl-8,9-diallyloxy-5,6-dihydro-phenan-thridine (11a);
4-ethenyl-5-methyl-8,9-di(prop-2-ynyloxy)-5,6-dihydro-phenanthridine (11b);
4-ethenyl-5-methyl-8,9-bis-cyclobutylmethoxy-5,6-di-hydro-phenanthridine (11c);
4-ethenyl-5-methyl-8,9-bis-cyclohexylmethoxy-5,6-di-hydro-phenanthridine (11d);
4-ethenyl-5-methyl-8,9-dibenzyloxy-5,6-dihydro-phenanthridine (11e);
4-ethenyl-5-methyl-8,9-di(2,3-dimethoxy)benzyloxy-5,6-dihydro-phenanthridine (11 f);
4-ethenyl-5-methyl-8,9-di(4-cyano)benzyloxy-5,6-di-hydro-phenanthridine (11g);
4-ethenyl-5-methyl-8,9-dibenzoyloxy-5,6-dihydro-phenanthridine (11m);
4-ethenyl-5-methyl-8,9-di(4-bromo)benzoyloxy-5,6-di-hydro-phenanthridine (11n);
4-ethyl-5-methyl-8,9-bis[1-(2-amino-ethyl)-1H-[1,2,3]triazol-4-ylmethoxy]-5,6-dihydro-phenanthridine (10q);
4-ethyl-5-methyl-8,9-bis[1-(2-acetylamino-ethyl)-1H-[1,2,3]triazol-4-ylmethoxy]-5,6-dihydro-phenanthridine (10r);
4-ethenyl-5-methyl-8,9-bis[1-(2-amino-ethyl)-1H-[1,2,3]triazol-4ylmethoxy]-5,6-dihydro-phenanthridine (11q); and
4-ethenyl-5-methyl-8,9-bis[1-2(acetylamino-ethyl)-1H-[1,2,3]triazol-4-ylmethoxy]-5,6-dihydro-phenanthri-dine (11 r).

6. A pharmaceutical composition, comprising a prophylactically or therapeutically effective amount of the compound according to claim 1 and a pharmaceutically acceptable carrier or excipient.

7. The compound of general formula (1) according to claim 1, wherein $R_3$ or $R_4$ is selected from

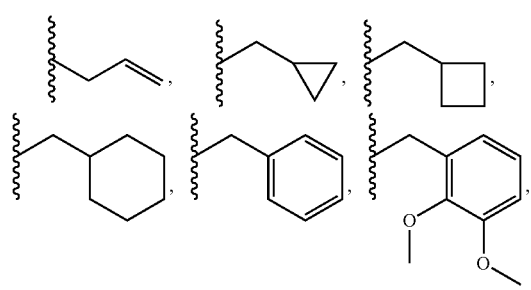

-continued

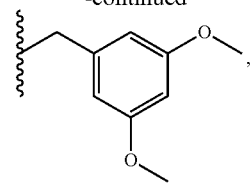

tert-butyldimethylsilyl, trimethylsilyl,

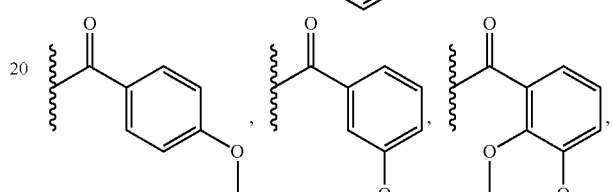

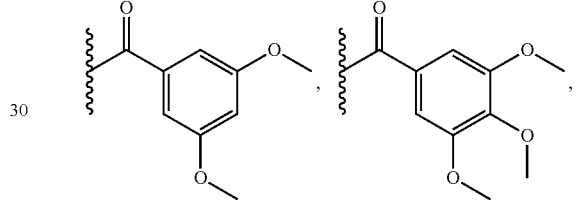

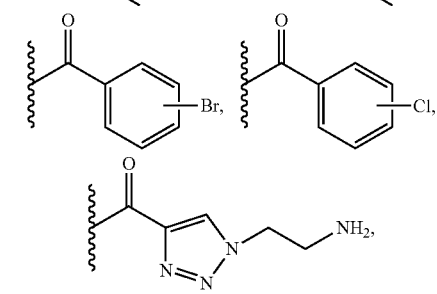

8. A pharmaceutical composition, comprising a prophylactically or therapeutically effective amount of the compound according to claim 5 and a pharmaceutically acceptable carrier or excipient.

* * * * *